(12) United States Patent
Keith

(10) Patent No.: US 8,926,571 B1
(45) Date of Patent: Jan. 6, 2015

(54) HEMODIALYSIS CATHETER ASSEMBLY

(76) Inventor: Clifford A. Keith, Olympia, WA (US)

(*) Notice: Subject to any disclaimer, the term of this patent is extended or adjusted under 35 U.S.C. 154(b) by 613 days.

(21) Appl. No.: 13/068,281

(22) Filed: May 6, 2011

(51) Int. Cl.
*A61M 5/00* (2006.01)
*A61M 5/178* (2006.01)
*A61M 25/16* (2006.01)
*A61M 39/28* (2006.01)

(52) U.S. Cl.
CPC .................................. *A61M 39/284* (2013.01)
USPC ........................ 604/250; 604/533; 604/167.01

(58) Field of Classification Search
CPC ..... A61M 39/26; A61M 39/10; A61M 39/22; A61M 25/0606; A61M 25/0097; A61M 2005/1585; A61M 2039/267; A61M 2039/1027; A61M 2039/268; A61M 25/0637; A61M 39/1011
USPC .......... 604/167.01, 168.01, 533, 167.02, 905, 604/164.01, 256, 537, 250, 161, 167.04, 604/167.05, 247, 164.13, 246, 249, 158, 604/164.02, 167.03, 167.06, 30, 34; 251/7, 251/9, 10, 115, 251, 4
See application file for complete search history.

(56) References Cited

U.S. PATENT DOCUMENTS

| | | | | |
|---|---|---|---|---|
| 3,856,010 A | * | 12/1974 | Moorehead et al. | 604/167.01 |
| 3,875,938 A | * | 4/1975 | Mellor | 604/167.01 |
| 4,046,144 A | * | 9/1977 | McFarlane | 604/168.01 |
| 4,429,852 A | * | 2/1984 | Tersteegen et al. | 251/9 |
| 4,540,411 A | * | 9/1985 | Bodicky | 604/167.05 |
| 4,960,259 A | * | 10/1990 | Sunnanvader et al. | 251/7 |
| 4,986,814 A | * | 1/1991 | Burney et al. | 604/164.11 |
| 5,108,374 A | * | 4/1992 | Lemieux | 604/167.01 |
| 5,108,380 A | * | 4/1992 | Herlitze et al. | 604/533 |
| 5,127,626 A | * | 7/1992 | Hilal et al. | 251/149.1 |
| 5,156,596 A | * | 10/1992 | Balbierz et al. | 604/164.11 |
| 5,281,206 A | * | 1/1994 | Lopez | 604/533 |
| 5,334,157 A | * | 8/1994 | Klein et al. | 604/160 |
| 5,749,857 A | * | 5/1998 | Cuppy | 604/164.12 |
| 7,252,652 B2 | | 8/2007 | Moorehead et al. | |
| 7,854,731 B2 | * | 12/2010 | Rome et al. | 604/540 |
| 8,043,280 B2 | * | 10/2011 | Bierman | 604/535 |
| 8,070,731 B2 | * | 12/2011 | Wenchell et al. | 604/167.06 |
| 2002/0161333 A1 | * | 10/2002 | Luther | 604/167.01 |
| 2008/0039796 A1 | | 2/2008 | Nakajima | |
| 2009/0281524 A1 | * | 11/2009 | Scheibe et al. | 604/528 |
| 2009/0281525 A1 | | 11/2009 | Harding et al. | |
| 2010/0168718 A1 | * | 7/2010 | Bellisario et al. | 604/533 |

* cited by examiner

*Primary Examiner* — Kevin C Sirmons
*Assistant Examiner* — William Carpenter
(74) *Attorney, Agent, or Firm* — Brian J. Coyne

(57) ABSTRACT

A hemodialysis catheter assembly with a flexible catheter lead that can control blood flow at a hemodialysis access site even under high blood pressures encountered at such sites. Flexible tubing extends through the hollow interior of a housing having opposite, open ends. The assembly includes components to alternately occlude or not occlude the lumen of the flexible tubing. In a first embodiment, spring clips press against the tubing, but insertion of a hollow sleeve into the lumen thereof retracts the clips and provides a flow path. In a second embodiment, a pinch bar can be manually moved into and out of engagement with the flexible tubing to occlude or open a flow path. In a third embodiment, the housing has a screw cap. A spring-loaded pinch bar presses against, and occludes the lumen of, the collapsible tubing when the screw cap is screwed into a threaded cutout in the housing, and provides a flow path through the tubing when the screw cap is removed. In a fourth embodiment, the tang portion of a tongue when in an extended position presses against, and occludes the lumen of, the compressible tubing; advancement of a capture ring attached to a sliding button retracts the tang portion and opens a flow path.

5 Claims, 15 Drawing Sheets

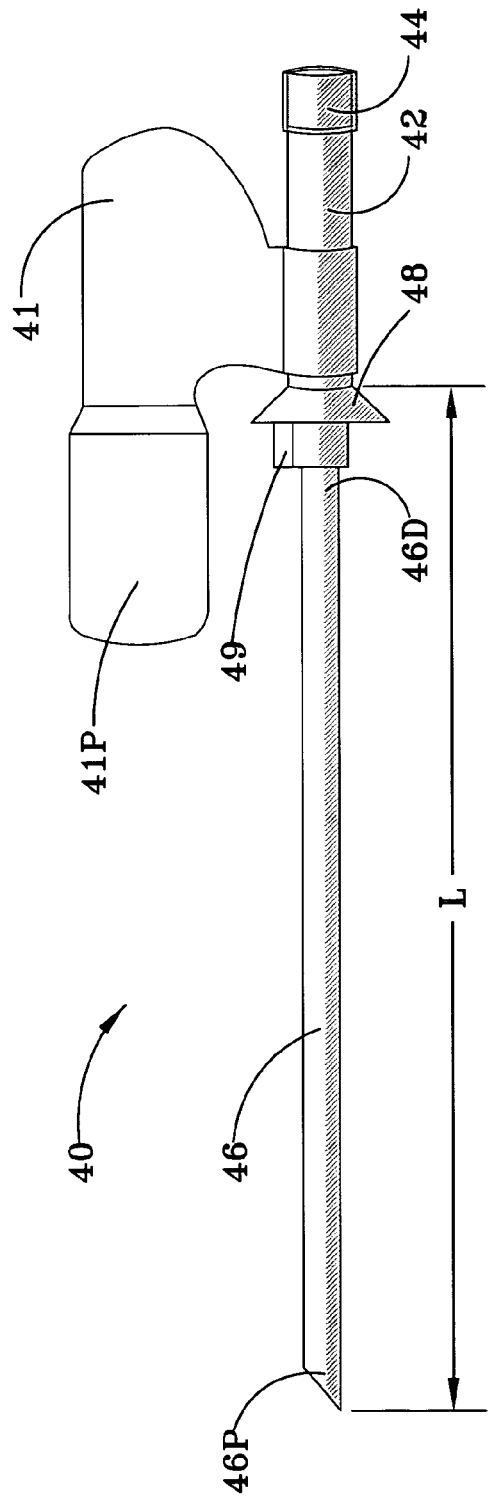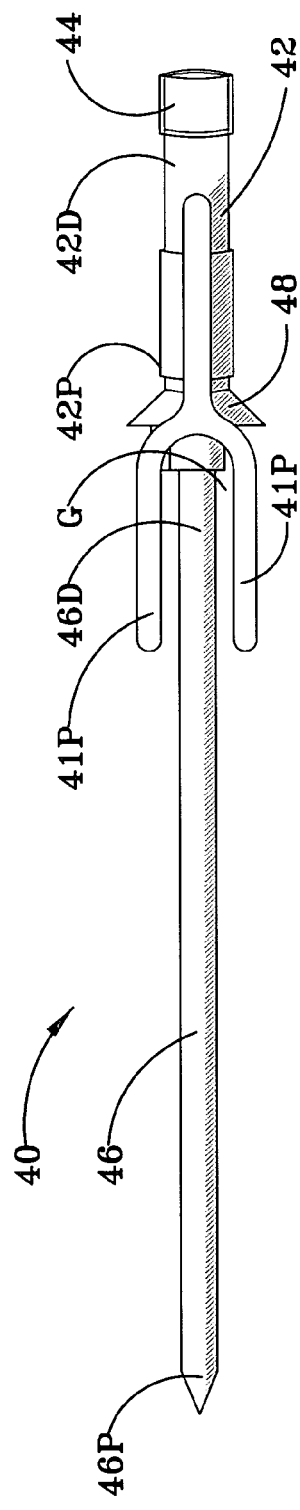
FIG. 4
FIG. 5

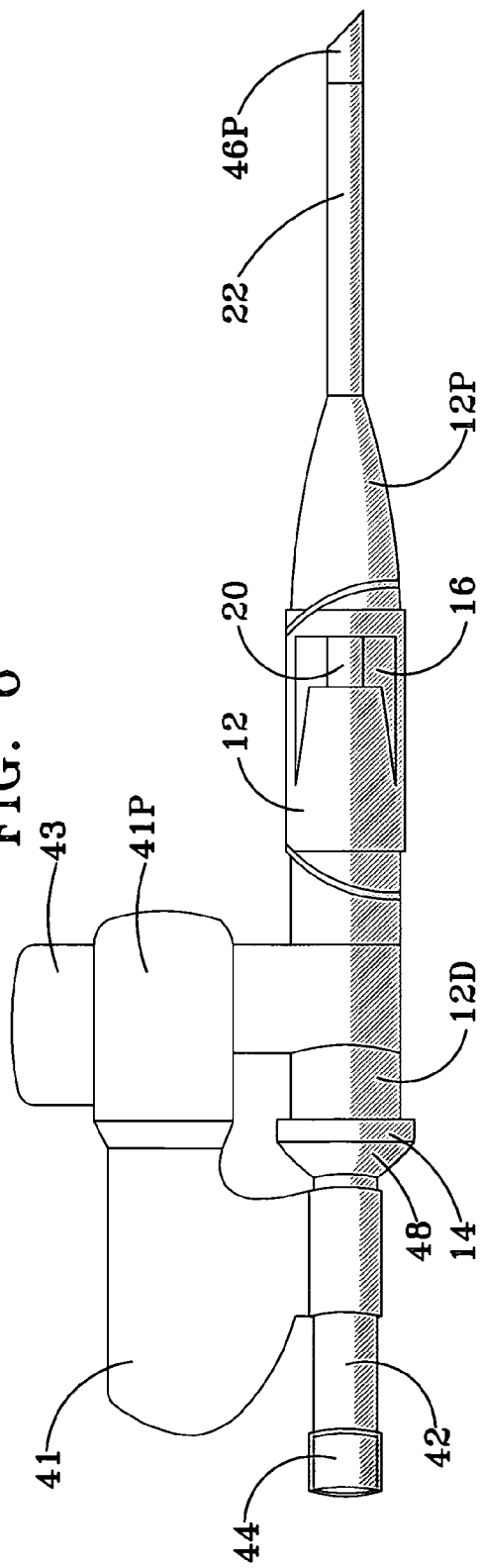
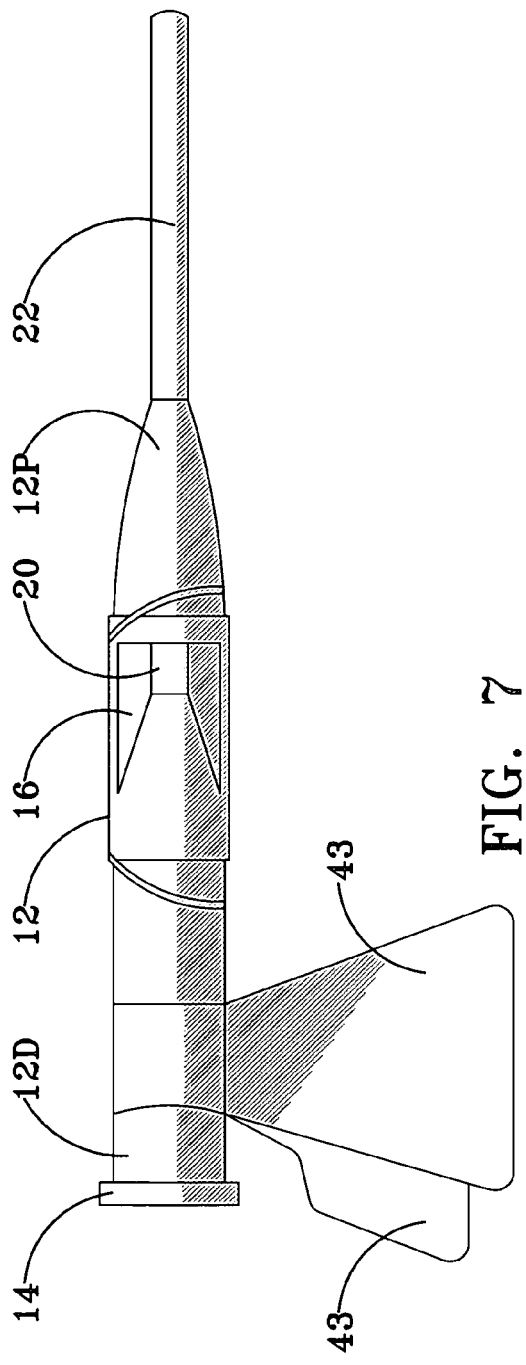

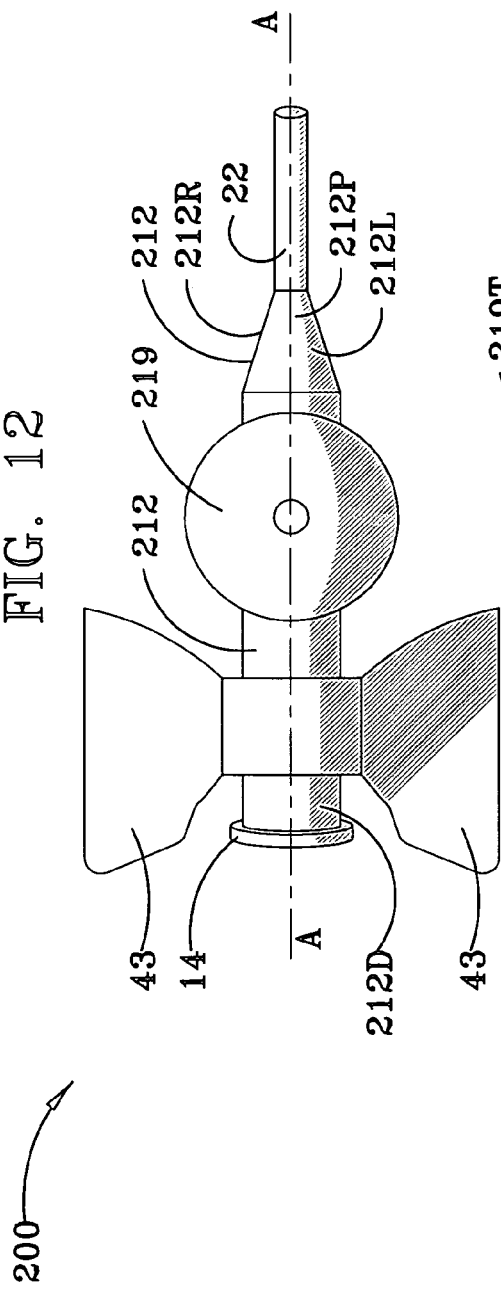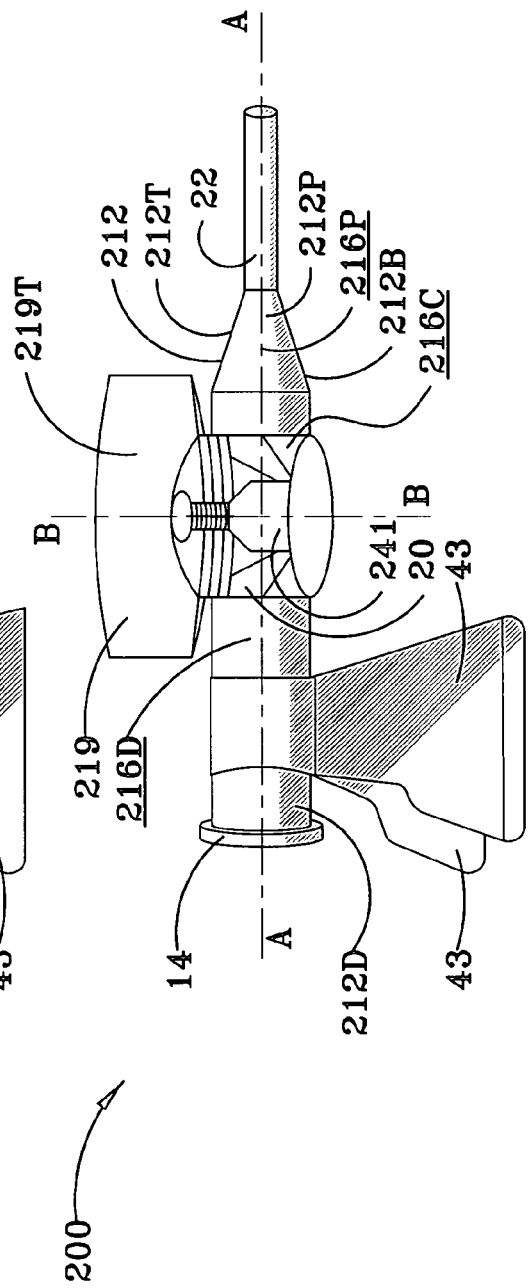

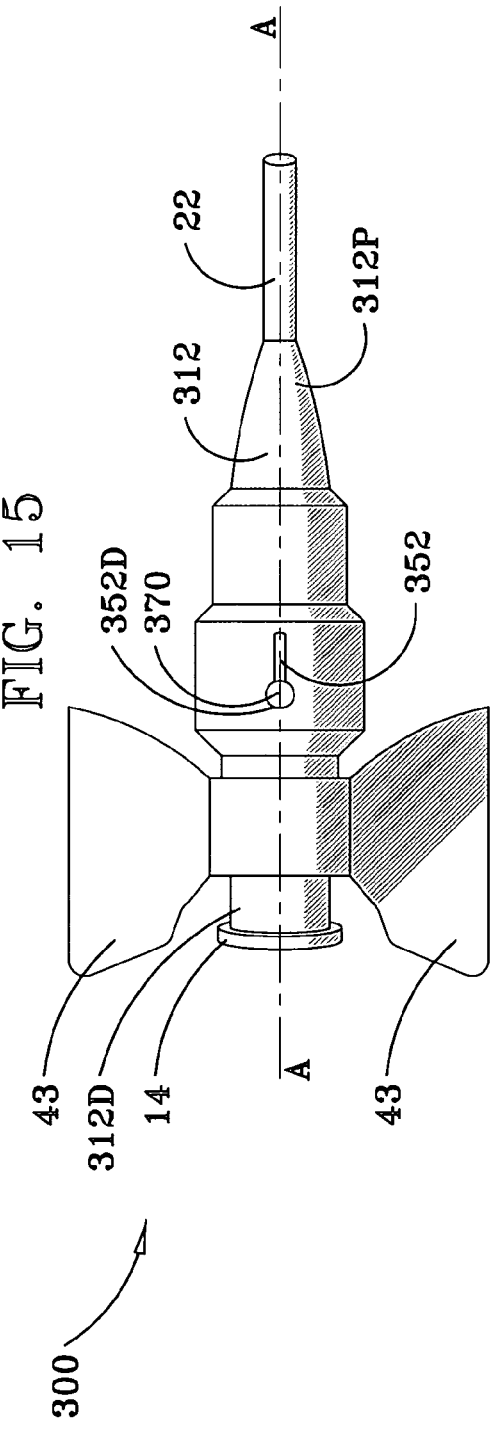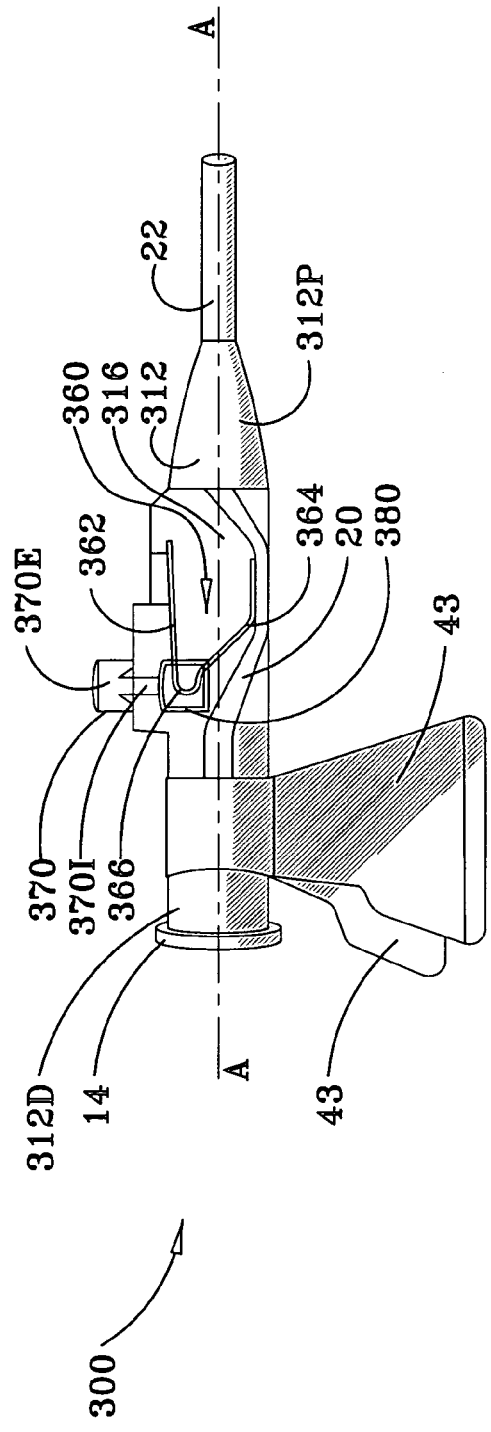

HEMODIALYSIS CATHETER ASSEMBLY

CROSS-REFERENCE TO RELATED PATENT APPLICATIONS

None

STATEMENT REGARDING FEDERALLY APPROVED RESEARCH OR DEVELOPMENT

None

BACKGROUND OF THE INVENTION

1. Field of the Invention

This invention relates to the field of medical devices. More particularly, this invention relates to an indwelling catheter assembly for use in hemodialysis.

2. Background Art

Hemodialysis catheters are used to remove waste products such as potassium and urea from the blood, such as in the case of a patient with renal failure. A first catheter conducts blood away from the patient through dialysis extension tubing to a dialysis machine where the blood crosses a semipermeable dialysis membrane to a balanced salt solution, which purifies the blood. A second catheter conducts the purified blood back from the dialysis machine to the circulation of the patient. Thus, while undergoing dialysis, a patient's blood circulates not only through his/her own body, but also through the dialysis machine circuit comprising the first and second catheters, dialysis extension tubing and the machine itself. In hemodialysis, both the arterial and venous access catheters are threaded into the same high flow, high pressure access site, albeit at somewhat spaced apart locations therein. A hemodialysis site may be either an AV fistula or a graft. An AV fistula is a surgically created area, usually on a patient's forearm, where blood flows just beneath the surface of the skin at high pressure and speed. An AV fistula is created by joining an artery directly to a vein, thereby artificially bypassing the normal (low pressure) capillary blood system. This causes high pressure arterial blood to pour into a normally low pressure vein, which causes the vein to distend and grow much larger. During hemodialysis, both the arterial access catheter and the venous access catheter are inserted into the patient's AV fistula, but the arterial access catheter is placed four to five centimeters upstream from the latter. That arrangement prevents mixing of cleansed blood with uncleansed blood at the AV fistula because the cleansed blood that is returned from the dialysis machine back to the patient is thereby carried away from the uncleansed blood that is being drawn up into the dialysis machine. If a patient's veins are in poor condition, a graft may be used as a hemodialysis site instead. A graft comprises an artificially-created loop of a synthetic material, such as Gortex (registered mark), that joins an artery directly to a vein. As in the case of an AV fistula, a graft will also present high pressure, high flow blood at the patient's hemodialysis access site, and placement of the arterial access and venous access catheters is performed similarly to that for an AV fistula. The hemodialysis catheter assembly of the present invention is intended for use with patients who have an AV fistula access site as well as those who have a graft hemodialysis access site.

Prior to my invention, access to a patient for hemodialysis has been gained by use of a dialysis catheter of simple design, consisting of nothing more than a sharpened, hollow, stainless steel needle and its attached extension tubing. Kidney dialysis patients typically require three dialysis sessions each week, and each dialysis session usually lasts three to four hours. As a result, repeated access must be gained to the patient's blood circulation over periods of time extending sometimes for years, and there is necessarily a continuing concern to avoid damaging the patient's hemodialysis access sites with the conventional sharpened, hollow, stainless steel needles at those sites. This is all in contrast to an intravenous (IV) catheter, which consists of a sharpened, hollow, stainless steel needle inserted within the lumen of a flexible, Teflon® sleeve or cannula for attachment to low pressure venous blood flow. The hollow, sharpened, steel needle of an intravenous catheter is carefully advanced into a patient's vein. Then the hollow, steel needle portion of the IV catheter is withdrawn, and the remaining Teflon® cannula is connected to a set of external, intravenous tubing for its use as an IV access site. This leaves the flexible Teflon® cannula of the intravenous catheter in the place of a sharpened steel needle, thereby reducing damage to the walls of veins for patients receiving IV therapy. The normal procedure for placing an intravenous catheter is to withdraw the sharpened, hollow, steel needle from the lumen of its flexible Teflon® sleeve after the successful engagement (cannulation) of a vein. During the time that the needle has been withdrawn and before the catheter has been connected to intravenous tubing, the open end of the catheter is exposed to room air at normal atmospheric pressure. The greater pressure within the venous circulatory system causes blood to slowly trickle out from the open end of the catheter. Because pressures within the venous circulatory system are relatively low, not much blood is lost this way. It is a common practice to exert a bit of pressure from a gloved finger placed just above the site where the blood flows through the lumen of the intravenous catheter. This point of resistance stops the trickle of blood from leaving the open end of the catheter until a set of IV tubing can be connected to it.

It would be highly advantageous, therefore, when performing hemodialysis on a patient, to substitute the flexible, Teflon® cannula/sharpened, hollow needle combination that is used in IV therapy for the dialysis catheter that has heretofore been used to gain access to a patient's hemodialysis site. A hemodialysis catheter having a flexible Teflon® tip would cause less trauma to the walls of blood vessels for patients receiving multiple sessions of hemodialysis. Reducing damage to these access sites would help extend the sites' functional life spans, and would significantly reduce the frequency of access-related complications arising out of hemodialysis therapy. But, as a practical matter, such a substitution cannot be done because of the difference in the pressure of the blood at an intravenous access site compared to the pressure of the blood at a hemodialysis access site that connects to the arterial side of the patient's blood circulatory system, because the arterial side has relatively high blood pressure—i.e., five to six times higher than an intravenous access site. If one attempts to use an intravenous catheter as a hemodialysis catheter, the higher pressure encountered on the arterial side of a patient's blood circulatory system will cause blood to rush out from the open end of the catheter at high speed. This would obviously create a hazard for the healthcare workers, exposing them unnecessarily to the patient's blood and to possible contamination by blood-borne pathogens. Furthermore, patients who receive dialysis therapy are predisposed to a condition that limits their ability to produce red blood cells. This condition is related to the pathology of kidney failure, so that nearly all hemodialysis patients who require regular dialysis therapy must also carefully manage their red blood cell count. Excessive blood loss is of particular concern for patients on hemodialysis and must always be avoided. Accordingly, the practice of holding a gloved finger and applying pressure just above the site where blood flows through the lumen of a hemodialysis catheter on the arterial side of a patient's blood circulatory system, in an attempt to control bleeding through the catheter, would not arrest the flow of blood from the open end of such a catheter. The pressures within the lumen of the catheter would be too great to be overcome by such a simple mechanical procedure. Unlike an intravenous catheter connected to a low pressure, venous access site, the catheter connected to the arterial side of a hemodialysis patient would continue to bleed profusely until one managed somehow to connect it to hemodialysis tubing, and so to secure a closed circuit. In addition, physicians are averse to having any sort of pressure or occlusion placed over these specially created hemodialysis access sites. They are artificially made avenues of high pressure blood flow created surgically just beneath the surface of the skin, and as such they are far more prone to clotting, and therefore to ruin, than' any naturally formed blood vessel. Consequently, the practice of maintaining pressure over a hemodialysis access site in an attempt to control the loss of blood is to be avoided.

U.S. Pat. No. 7,252,652 B2 issued to Moorehead et al. disclosed a pressure-activated, two-way slit valve assembly for use in combination with a high flow rate, hemodialysis catheter. The valve assembly could be attached to a catheter having a single lumen or alternatively multiple lumens, and included a flexible, normally closed, thin disk disposed normal to the direction of blood flow through the assembly. The disk was sized to enable the slit to deform in response to a predetermined blood pressure differential across the slit to allow blood to pass through the slit, which flow could be either away from the patient toward a dialysis machine or toward the patient from a dialysis machine, depending upon the direction of the pressure differential.

Patent Application Publication US2009/0281525 A1 of Harding et al. disclosed a device with integrated flow control capabilities for controlling fluid flow through an indwelling catheter assembly, intended for use in artificial dialysis, among other applications. A catheter adapter body having a hollow, interior space or lumen was coupled to an end of a catheter. A flexible, normally-closed septum disposed within the interior space of the catheter body could be opened to permit flow through the catheter body by depressing an exterior, flow control button disposed within a window opening of the catheter body adjacent to the septum. In one embodiment, the septum comprised a normally-closed slit that could be opened to permit flow whenever the septum was inwardly deformed by depressing the button. Alternatively, insertion of a probe, such as a hollow needle, into the interior space of the catheter body and through the slit would also open the slit and permit flow through the catheter adapter body. In an alternative embodiment, the septum was impermeable and had no slit; instead, the septum was positioned within the lumen of the catheter adapter body so as to form a fluidtight interface between the septum and the inner surface of the catheter adapter body. Depressing a flow control button comprising a contact surface coupled to a shaft caused the shaft to displace the septum and disrupt the interface between the septum and the inner surface of the adapter body, thereby permitting fluid flow through the gap between the outer surface of the septum and the inner surface of the adapter body.

The above-referenced devices of Moorehead and of Harding et al. are not really suitable for use in hemodialysis because they fail to adequately address the problem of turbulence in blood flowing at high speed and under high pressure through the relatively small internal channel (lumen) within a dialysis catheter. Excessive turbulence can cause red blood cells to break open, rendering them useless to the patient and possibly contributing to electrolyte imbalances within the blood stream. To avoid turbulence, the internal surfaces of a hemodialysis catheter must be smooth, gradually tapered and seamlessly connected with one another.

Three of the four versions of the device disclosed by Harding et al. include ribbing on the surface of a septum actuator, which ribbing will create excessive turbulence within the body of their catheter. In an alternate version disclosed by Harding et al., the ribbing is absent, but the inner walls of the catheter gradually taper just past the point where a flexible septum crosses the lumen of the catheter and is joined together with the internal walls of the catheter body. This tapering would cause any probe capable of fitting within the catheter body and which is used to bias the septum to stop short of joining flush with the window that connects the septum chamber to the rest of the catheter body and its extension lead. The failure of such a probe to join flush with this window will cause the inserted end of the probe to be exposed as an open step or open shelf within the lumen of the dialysis catheter. Blood rushing past this exposed shelf at high speed will be subjected to excessive turbulence.

Similarly, all five versions of the device disclosed by Moorehead fail to adequately address the problem of excessive turbulence. All five versions include multiple flow channels within a single lumen of a hemodialysis catheter. These include dumbbell-shaped, H-shaped, and saw tooth split channels. Such systems of narrow channels create excessively turbulent flow of blood through the lumen of a catheter under the high pressure, high speed flow conditions encountered at a hemodialysis access site. Furthermore, such systems of channels create high back pressure that slows the progress of filtration and circulation in a dialysis machine circuit.

Harding's device includes a push button disposed over the top of the hemodialysis catheter body, which must be pressed down in order to permit blood to flow through the catheter. Hard pressure applied to the button causes hard pressure to be applied over the surface of the hemodialysis access site. That is an unacceptable practice, as it is well known that such hard pressure can lead to complications with the access site itself.

The thin, dual membrane septum assembly disclosed by Harding et al., which is intended to permit blood flow in one direction only, is likely to weaken with use and begin to deform to permit blood flow in an opposite direction through the septum assembly. The result could be escape of blood through the open lumen of Harding's dialysis catheter just as easily as blood could enter into it.

My hemodialysis catheter assembly, however, avoids these problems. It is capable of reliably arresting blood flow even under high pressure, high speed blood flow conditions and without creating excessive flow turbulence. It does not create back pressure within the dialysis machine circuit, and it does not create any unnecessary pressure or occlusion across the surface of a hemodialysis access site.

SUMMARY OF THE INVENTION

Thus, there remains a need for a hemodialysis catheter assembly that provides a catheter having a flexible catheter tip in order to reduce trauma to the walls of a patient's blood vessels and to reduce other access-related complications heretofore associated with hemodialysis. There further remains a need for such an assembly that provides a normally closed pathway for flow of blood, such as for those times when a clinician is in the process of attaching the catheter to a patient's hemodialysis access, and which pathway can be manually opened by the clinician in a controlled manner to permit blood flow in a way that avoids uncontrolled bleeding or loss of the patient's blood—even under the relatively high pressures that are encountered when the catheter is connected to the arterial side of a patient's blood circulatory system. The instant invention provides these and other features and advantages that will become apparent from the detailed description and drawings set forth below.

To achieve these features and advantages, the invention provides a hemodialysis catheter assembly. The assembly includes a housing that extends along a longitudinal axis A-A from an open, proximal end to an opposite, open, distal end thereof. The housing has a hollow, interior space that communicates with the openings of its proximal and distal ends. Within the housing, a segment of collapsible tubing extends along axis A-A from a proximal end to an opposite, distal end thereof, which ends are attached to the housing. The collapsible tubing comprises a cylindrical wall that defines a lumen, which lumen communicates with the openings of the proximal and distal ends of the housing. The assembly further includes a flexible catheter lead, which lead has a distal end attached to the proximal end of the housing and an opposite, free, proximal end. The lumen of the flexible catheter lead communicates with the lumen of the collapsible tubing. A dialysis extension tubing subassembly couples to the distal, open end of the housing, and thereby permits incorporation of the housing into a dialysis machine circuit via said tubing.

For initial access to a hemodialysis site, a hemodialysis needle subassembly is provided. The needle subassembly includes a barrel that extends longitudinally from an open, proximal end to an opposite, open, distal end. The barrel has a hollow, interior space that communicates with its open, proximal and distal ends. A flashback chamber is attached to the distal end of the barrel. The flashback chamber comprises a cap that completely covers and closes off the distal end of the barrel. A semipermeable membrane within the chamber permits air, but not blood, to escape whenever blood enters into the chamber. At least a portion of the chamber is transparent in order to permit visual monitoring of entry of blood into the chamber. A hollow needle extends from a distal, open end to an opposite, proximal end comprising a sharpened, bevel point. An adapter joins the distal shaft of the needle with the open, proximal end of the barrel. The adapter has a longitudinal bore that extends from an open, proximal end to an open, distal end thereof. The distal shaft of the needle is fixed within the bore of said adapter. A distal portion of said adapter is continuous with the proximal portion of the barrel. The bore of said adapter is in alignment with the hollow interior of the barrel. The adapter is shaped and dimensioned for close fitting retention within the distal portion of the catheter housing. The adapter retains the shaft of the needle securely within the hollow, interior space of the catheter housing and aligned along axis A-A until after a clinician has successfully engaged the sharpened needle tip and its surrounding flexible catheter lead with a patient's hemodialysis access site. After this engagement (cannulation) has been made, the needle and adapter are withdrawn from the hollow, interior space of the housing. So long as the shaft of the needle is still within the hollow, interior space of the housing and aligned along axis A-A, the proximal, sharpened end of the needle extends beyond the proximal end of its surrounding catheter lead, and the opposite, distal end of the needle is inserted into, and retained within, the proximal end of the bore of the adapter such that the lumen of the needle communicates with said bore and is in alignment with the hollow, interior space of the barrel and the attached flashback chamber.

Pinch means is positioned between the proximal and distal ends of the collapsible tubing and within the interior space of the housing. The pinch means is alterable between normally pinched conditions wherein a portion of the wall of the collapsible tubing is collapsed inwardly and sufficiently to occlude and prevent blood flow through said tubing, and an unpinched condition wherein the lumen of said tubing is not occluded.

In a first embodiment of the invention, the pinch means comprises a pair of spring clips attached to the housing and disposed on opposite sides of the collapsible tubing. The clips are movable between a first, normally-pinched position and a second, retracted position. When the clips are in the pinched position, the collapsible tubing is collapsed and the lumen thereof is occluded to prevent flow of blood; whereas, when the clips are in the retracted position, the lumen thereof is not occluded and blood can flow through the collapsible tubing.

In a second embodiment of the invention, the pinch means comprises a pinch bar that is mounted and movable within the housing between an extended position and a retracted position. In the extended position, the bar engages an exterior surface of the collapsible tubing with sufficient force to collapse the tubing, occlude the lumen thereof, and thereby prevent blood flow through the tubing; whereas, in the retracted position, the pinch bar is disengaged from the collapsible tubing, the tubing is not collapsed, the lumen of the tubing is not occluded, and blood can flow through the collapsible tubing.

In a third embodiment of the invention, the housing has vertically spaced-apart bottom and top walls joined by laterally spaced apart left and right side walls. These walls in combination define a hollow, distal interior space, a hollow, proximal interior space and, joining and in communication with the proximal and distal interior spaces, a hollow, substantially cylindrical, central interior space. The central interior space is aligned along a transverse axis B-B that is normal to axis A-A and extends from the lower wall to the top wall. The top wall has a circular cutout centered on and normal to the axis B-B, which cutout has an internal thread. A screw cap is provided for covering the circular cutout of the housing, which cap has an external thread for mating engagement with the internal thread of the circular cutout. The pinch means includes a pinch bar that is mounted and movable within the housing between an extended position and a retracted position. The pinch bar includes a stop block. A coil spring, aligned along axis B-B, surrounds the pinch bar and extends from the stop block up to a lower portion of the screw cap and through a flange portion thereof. In its extended position, the pinch bar, urged by the coil spring, engages an exterior surface of the collapsible tubing and forces the tubing against the bottom wall of the housing, which collapses the tubing and occludes the lumen of the tubing; whereas, in its retracted position, the pinch bar is disengaged from the collapsible tubing sufficiently that said tubing is not collapsed, and the lumen of said tubing is not occluded.

In a fourth embodiment of the invention, the pinch means includes a tongue and mounting means attached to the housing for mounting the tongue within the interior space of the housing adjacent to the collapsible tubing. The tongue comprises a mounting portion and a flexible, resilient, tang portion. The tang portion is movable between an extended position and a retracted position. In its extended position, the tang portion engages an exterior surface of the collapsible tubing with force sufficient to collapse and occlude said tubing; whereas, in its retracted position, the tang portion is disengaged from the collapsible tubing and said tubing is not collapsed and the lumen of said tubing is not occluded. Latch means is provided that alternately retains the tang portion in its retracted position and releases the tang portion from its retracted position to permit the tang portion to resume its extended position. In a preferred version of the fourth embodiment, the housing has a slotted opening that extends parallel to axis A-A, which slotted opening has a proximal end and an opposite, distal end. The tang portion is longitudinally extended in a direction substantially parallel to axis A-A, but is progressively sloped along the length thereof toward the collapsible tubing. The mounting means comprises a button slidably mounted within the slotted opening for movement in a first direction and in a second, opposite direction, between the proximal and distal ends of the slotted opening. The button has an exterior portion that is disposed exterior to the housing and an opposite, interior portion that extends into the interior space of the housing toward the collapsible tubing. Attached to the interior portion of the button is a capture ring. The capture ring is disposed, shaped and dimensioned to alternately move into, and out of, surrounding engagement with the tang portion of the tongue as the button is moved from one end to an opposite end of the slotted opening. As the capture ring moves into surrounding engagement with the tongue, the tang portion thereof progressively retracts away from the collapsible tubing, which permits blood flow through said tubing; whereas, as the capture ring moves out of surrounding engagement with the tongue, the resilient force of the tang portion progressively forces collapse of the collapsible tubing and occludes the lumen thereof, thereby progressively blocking blood flow through the collapsible tubing.

BRIEF DESCRIPTION OF THE DRAWINGS

FIG. 4 is left side, elevational view of the needle subassembly thereof;

FIG. 5 is a top plan view of the needle subassembly thereof;

FIG. 6 is a right side, elevational view of the first embodiment of the invention as it would appear upon delivery from a manufacturer and after being removed from sterile packaging (not shown), ready for use on a hemodialysis patient; and FIG. 7 is a right side, elevational view thereof after withdrawal of the needle subassembly;

FIG. 12 is a top plan view of a third embodiment of the invention;

FIG. 13 is a right side, elevational view thereof, showing the body partially cut away.

FIG. 15 is a top plan view of a fourth embodiment of the invention; and

FIG. 16 is a right side, elevational view thereof, showing the body partially cutaway and collapsible tubing therein engaged and collapsed by the tang portion of a tongue that is in an extended position.

DETAILED DESCRIPTION OF THE INVENTION

Figure 1:
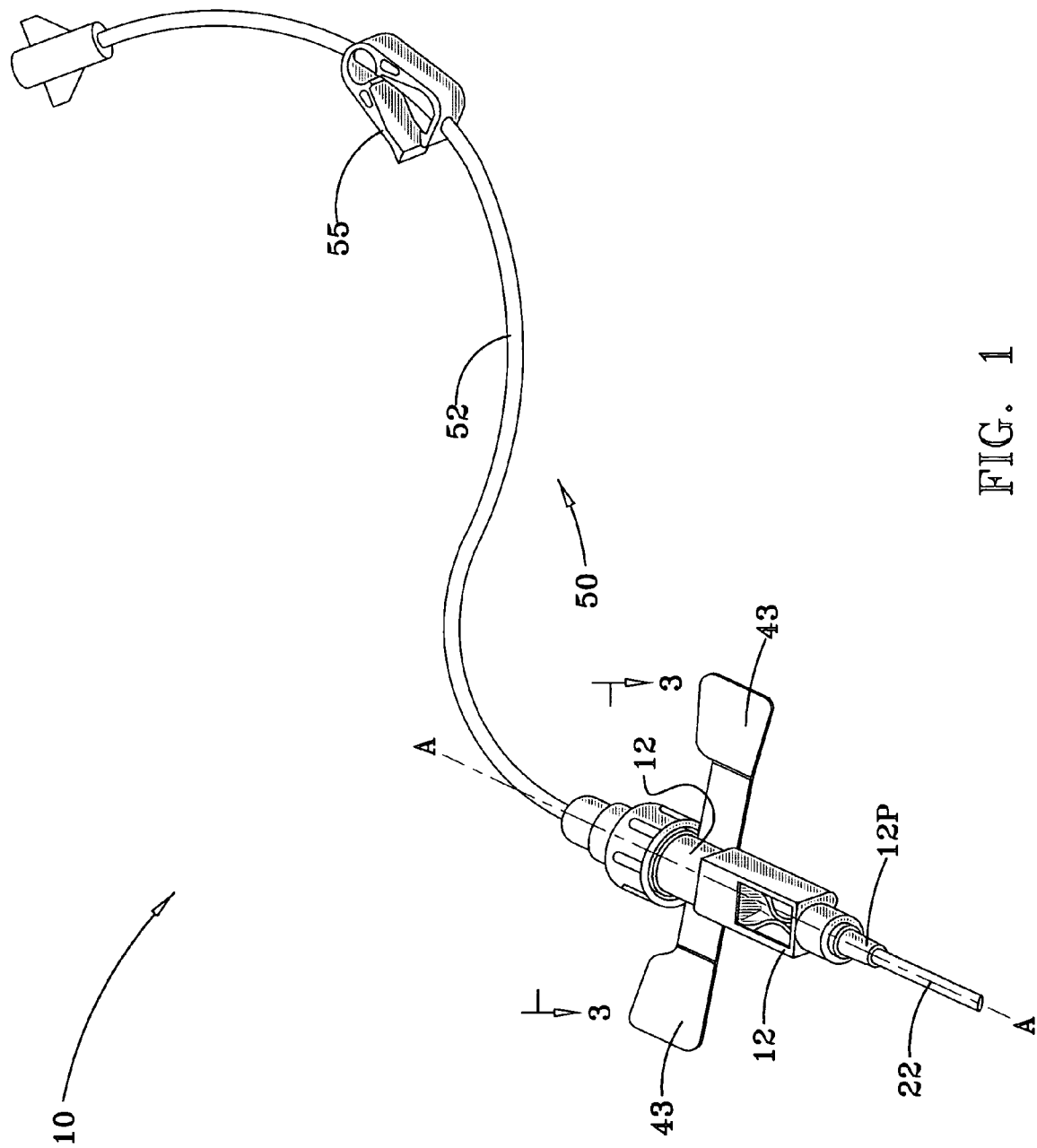
FIG. 1 is a perspective view from above of a first embodiment of the invention.
Figure 2:
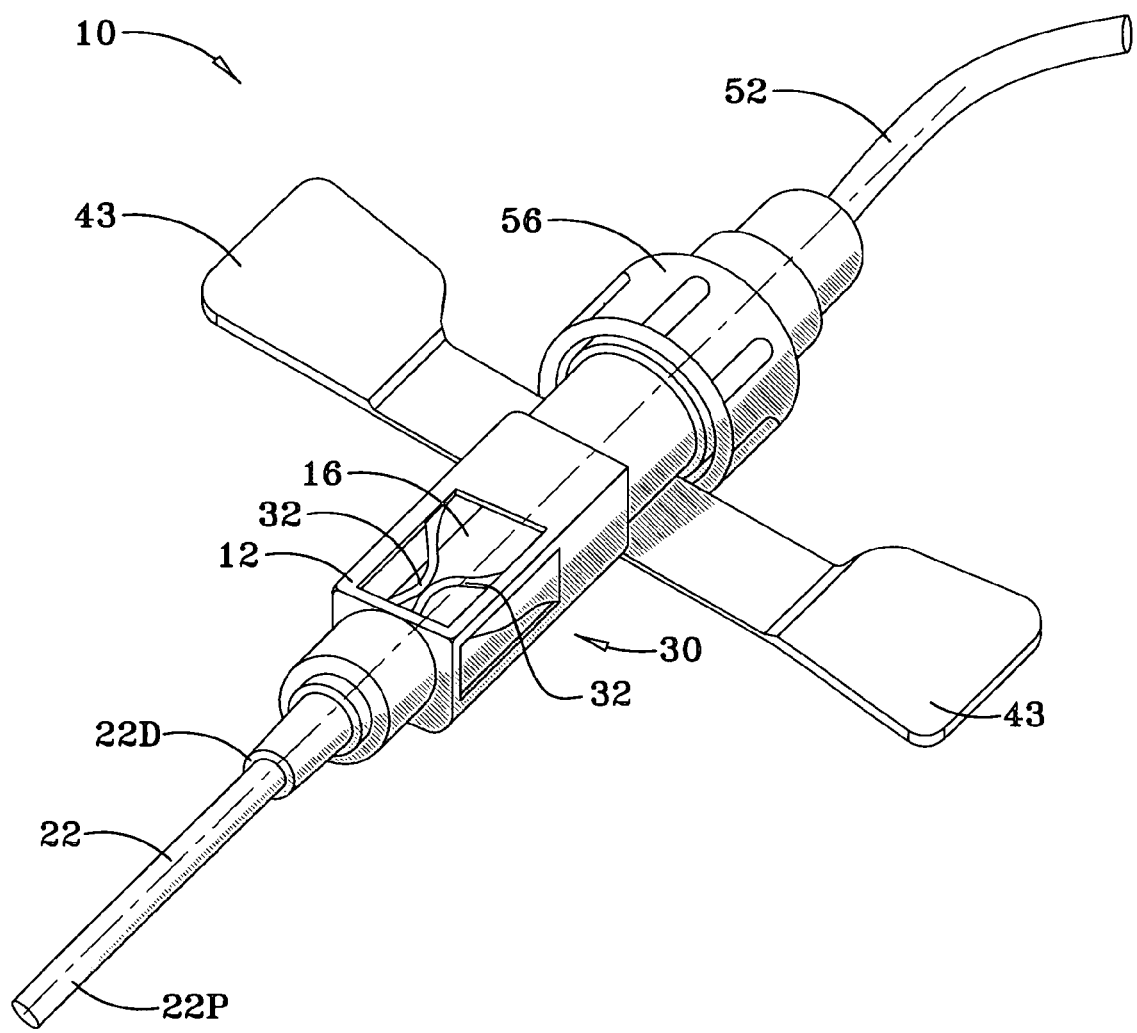
FIG. 2 is an enlarged, perspective view thereof, with the housing partially cutaway to show spring clips within the interior space thereof, and collapsible tubing omitted for clarity.

A first embodiment of the present invention will be described hereinafter with respect to the drawings. Throughout the description of this first embodiment, as well as of the other embodiments of the invention discussed below, the term "proximal" when applied to some component or aspect of the invention should be understood to mean that the component or aspect of the invention is relatively near to a patient's hemodialysis access site when the invention is in use, and the term "distal" should be understood to mean it is relatively remote from said site. FIG. 1 depicts a hemodialysis catheter assembly according to the first embodiment of the invention, denoted generally by the numeral 10, its sterile packaging (not shown) having been removed, and ready for use in hemodialysis. With further reference to FIGS. 2-9, it may be seen that the assembly 10 includes a housing 12 that extends along a longitudinal axis A-A from an open, proximal end 12P to an opposite, open, distal end 12D thereof; a first, externally-threaded screw lock 14 that is attached to, and circumposed about, the distal end 12D of the housing, and a dialysis extension tubing subassembly 50 (FIG. 8) that couples to said screw lock, in a manner described below. The housing 12 has a hollow, interior space 16 that communicates with the openings at the proximal end 12P and the distal end 12D thereof. Collapsible tubing 20 extends along axis A-A within the interior space 16 of the housing 12 from a proximal end 20P to an opposite, distal end 20D thereof. The proximal end 20P and the distal end 20D of the collapsible tubing 20 are attached to the proximal end 12P and the distal end 12D of the housing 12, respectively, by an adhesive (not shown). The collapsible tubing 20 comprises a cylindrical wall that defines a lumen, which lumen communicates with the openings of the proximal end 12P and distal end 12D of the housing 12. A flexible, catheter lead 22 extends longitudinally along axis A-A from a proximal, free end 22P to an opposite, distal end 22D and is preferably comprised of Teflon®. The distal end 22D of the catheter lead 22 is inserted into, and attached to, the open, proximal end 12P of the housing 12. The proximal end 22P of the catheter lead 22 protrudes from the proximal end 12P of the housing 12 proximally a distance of 2 to 4 centimeters, more or less.

Figure 3:
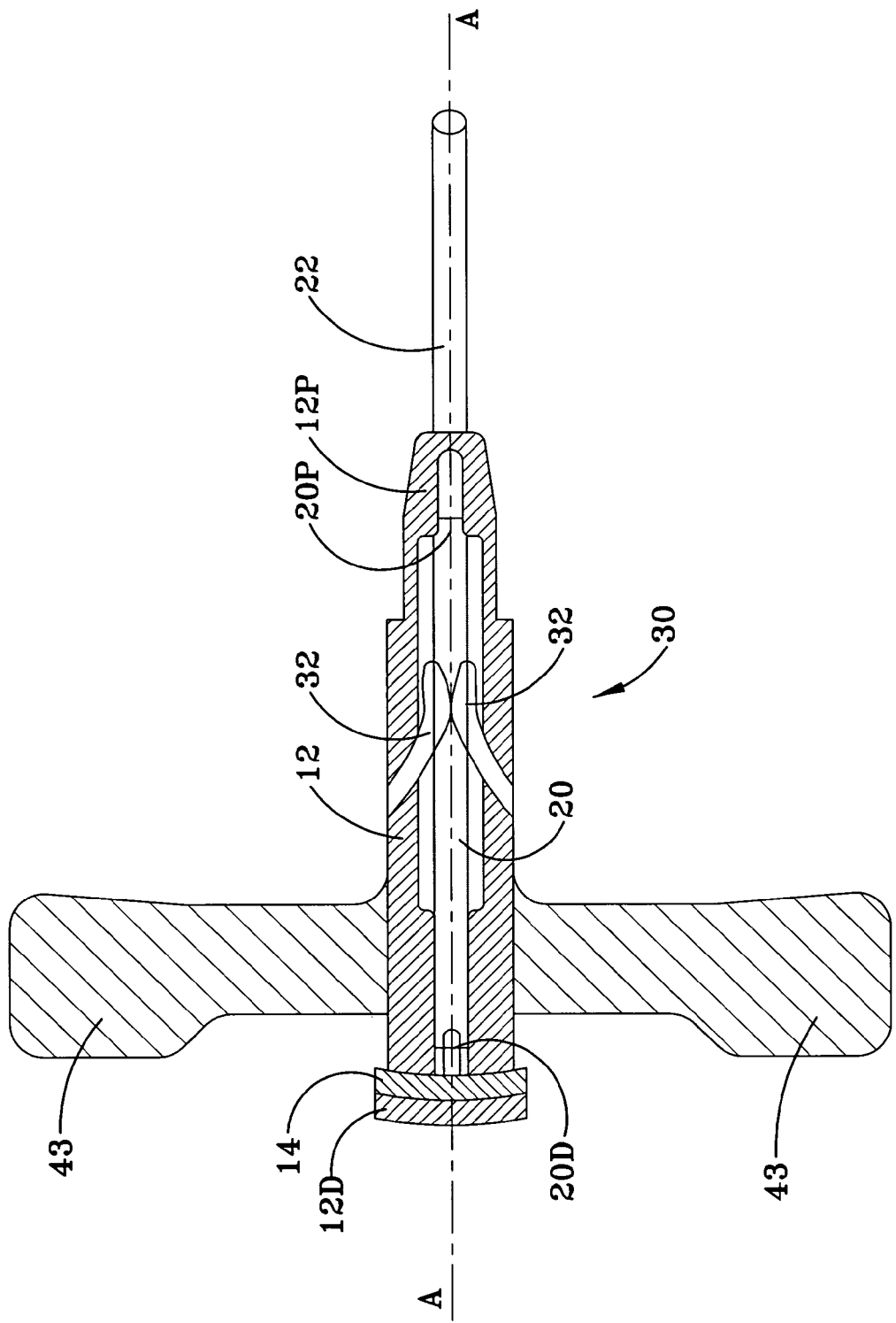
FIG. 3 is a further enlarged, cross-sectional view thereof taken along line 3-3 of FIG. 1.

The hemodialysis catheter assembly of the present invention further includes pinch means, denoted generally by the numeral 30, disposed intermediate the proximal end 20P and the distal end 20D of the collapsible tubing 20 and within the interior space 16 of the housing 12. The pinch means 30 is alterable between a normally pinched condition, wherein a portion of the wall of the collapsible tubing 20 is collapsed inwardly and sufficiently to occlude the lumen and prevent blood flow through the tubing, and an unpinched condition wherein the tubing is not collapsed and the lumen thereof is not occluded. In the first embodiment 10, the pinch means 30 includes a pair of resilient, spring clips 32, 32 within the interior space of 16 of the housing 12, attached to the housing and disposed on opposite sides of the collapsible tubing 20. As installed within the housing 12, and as shipped from the factory of manufacture, the clips 32, 32 are pre-stressed so that they press toward each other and against opposite sides of the collapsible tubing 20 with force sufficient to collapse said tubing, occlude the lumen thereof, and prevent blood flow; whereas, axial insertion of a sharpened, hollow, stainless steel needle 46 through the collapsible tubing 20 forces the clips apart and permits blood flow, as described more fully below. The spring clips 32, 32 preferably are cantilever springs, the free ends of which forcibly engage opposite sides of the collapsible tubing 20, as depicted in FIG. 3.

Figure 19:
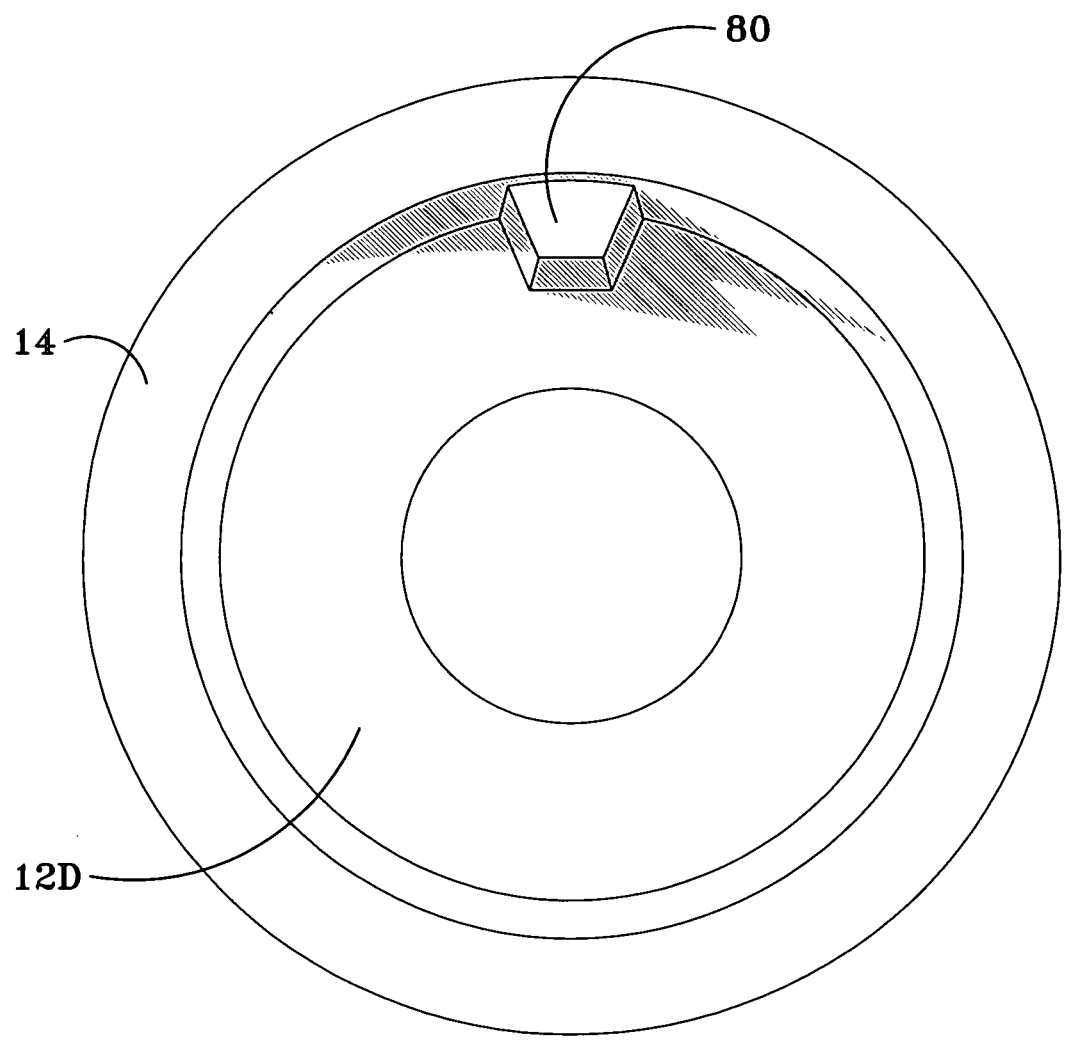
FIG. 19 is an enlarged, elevational view of a distal, open end of the housing of all four embodiments of the invention.

A hemodialysis needle subassembly, denoted generally by the numeral 40, is depicted separately in FIGS. 4 and 5, as it would appear upon delivery from a manufacturer thereof and after being removed from sterile packaging (not shown), ready for use. The needle subassembly 40 includes a barrel 42 that extends longitudinally from an open, proximal end 42P to an opposite, open, distal end 42D and has a hollow interior space that communicates with the open proximal and distal ends thereof. A hollow, flashback chamber 44 is axially aligned with, and attached to, the distal end 42D of the barrel 42 and comprises a cap that completely covers and closes off the distal end of the barrel. The chamber 44 has a semipermeable membrane (not shown) to permit air, but not blood, to escape from the chamber whenever blood enters into the chamber. The membrane may comprise a porous cotton weave or any other material that is permeable to air flow but not to blood flow. At least a portion of the chamber 44 is transparent to light to permit visual monitoring of entry of blood into the chamber. The needle subassembly 40 further includes a hollow, stainless steel needle 46 that has a proximal end 46P comprising a sharpened, bevel point, and an opposite, distal end 46D; and an adapter 48 for coupling the distal end 46D of the needle 46 to the open, distal end 12D of the housing 12. The adapter 48 extends longitudinally from a proximal end to an opposite distal end thereof, and has a longitudinal bore that extends from said proximal end to said distal end. The proximal end of the adapter 48 is shaped and dimensioned for close fitting retention with the open, distal end 12D of the catheter housing 12, and the distal end of the adapter 48 is permanently attached to, and continuous with, the proximal end 42P of the barrel 42. As may be seen in FIG. 4, a raised lug 49 extends from a proximal portion of the adapter 48 and is dimensioned for sliding insertion into, and retention within, an open-ended, shallow, longitudinal groove 80 (FIG. 19) that extends proximally from the open, distal end 12D of the housing 12 along an interior surface therein. Accordingly, the needle subassembly 40, when coupled to the distal end 12D of the housing 12, is prevented from rotating about axis A-A with respect to the housing. So long as the needle subassembly 40 is coupled to the housing 12, the distal end 46D of the needle 46 is inserted into, and retained within, the proximal end of said bore, and the needle 46 extends proximally away from the adapter 48 a distance L that exceeds the combined axial length of the housing 12 and the length of the flexible catheter lead 22 so that the sharpened needle point 46P protrudes through and somewhat beyond the proximal end of the catheter lead so long as the needle subassembly 40 remains coupled to the housing 12. So coupled, the lumen of the needle 46 communicates with the bore of the adapter 48 and is aligned with the flashback chamber 44, and the bore of the adapter 48 communicates with the hollow, interior space of the barrel 42. The needle subassembly 40 preferably further includes an upstanding finger grip 41 attached to the barrel 42 to facilitate maneuvering the needle 46 into engagement with an access site on the body of a hemodialysis patient. In a preferred version of the first embodiment, a pair of laterally and oppositely directed, flexible wings 43 are attached to the housing 12 to facilitate attaching the housing to a hemodialysis patient adjacent to a hemodialysis access site—for example, by adhesive tape. The proximal portion 41P of the finger grip 41 is bifurcated to define a pair of laterally spaced apart prongs and a gap G therebetween for storing the wings 43 folded together in the gap when they are not in use; compare FIG. 6 (wings folded and stored) with FIG. 7 (wings unfolded and deployed).

Figure 8:
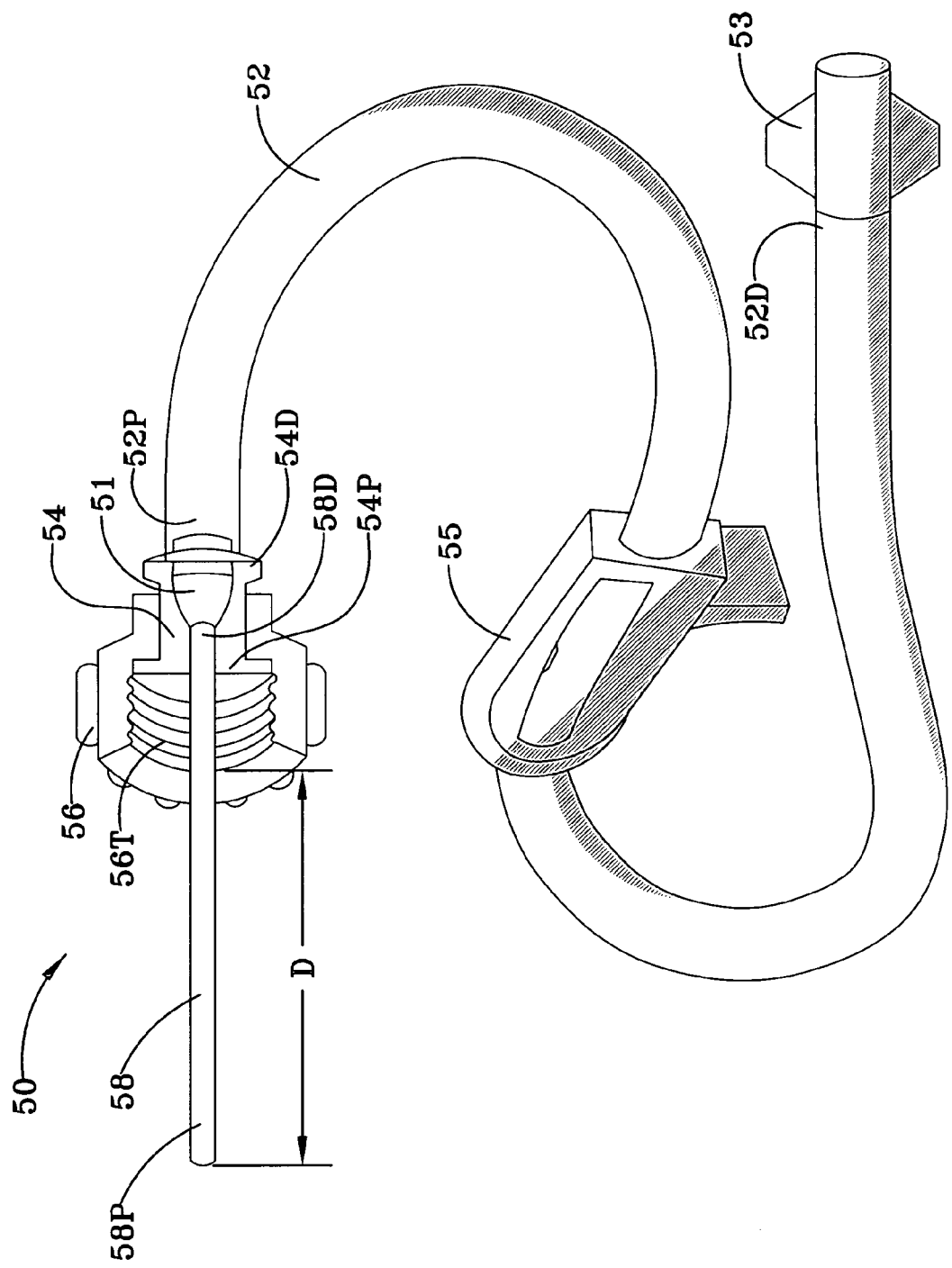
FIG. 8 is a perspective view of the dialysis extension tubing subassembly of the first embodiment of the invention, shown uncoupled from the housing.
Figure 9:
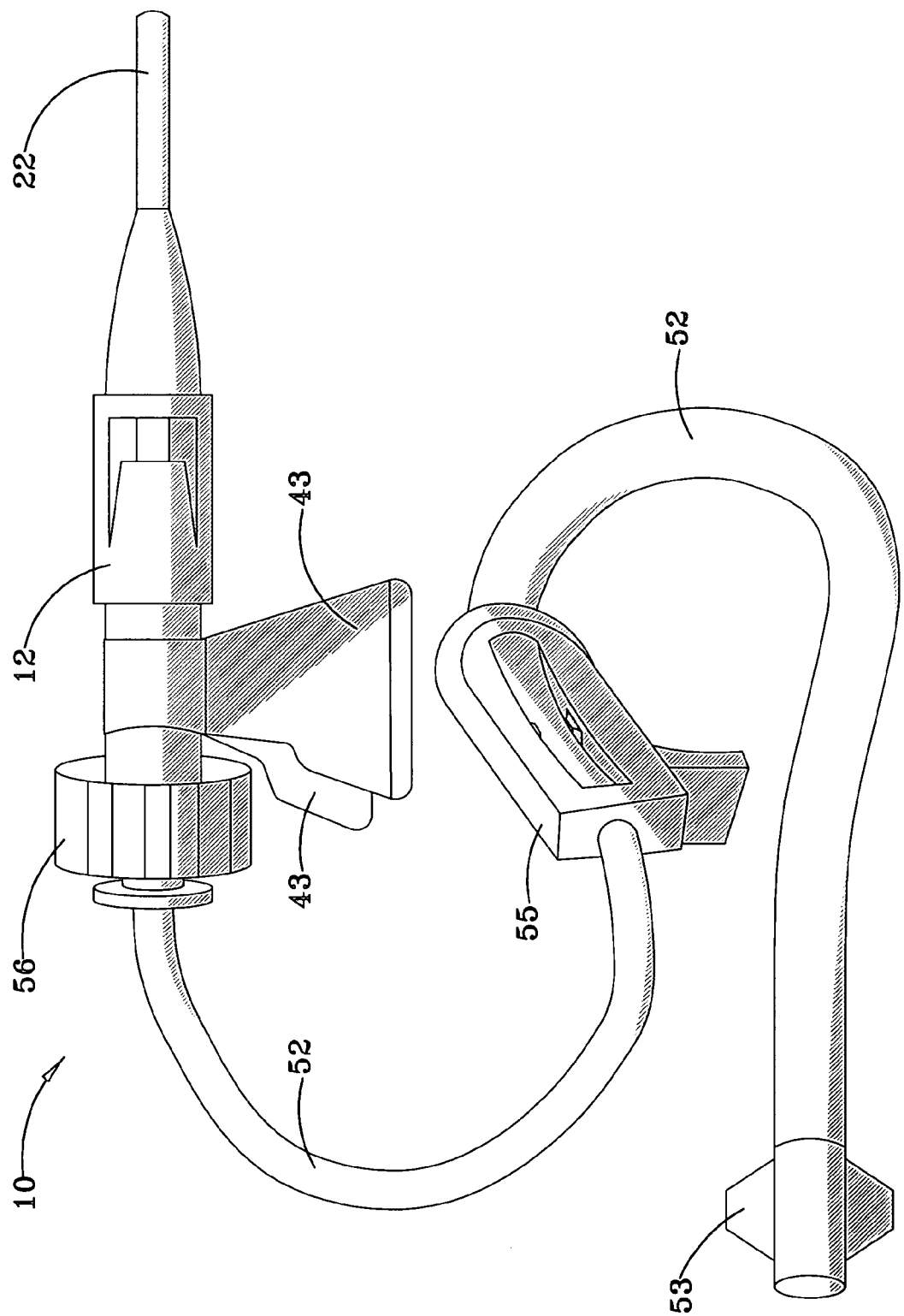
FIG. 9 is a right side, perspective view of the first embodiment of the invention, showing the dialysis extension tubing subassembly coupled to a distal, open end of the housing.

Referring now to FIG. 8, the first embodiment 10 further includes a dialysis extension tubing subassembly 50, which can be coupled to, and uncoupled from, the open, distal end 12D of the housing 12. The extension tubing subassembly 50 includes dialysis extension tubing 52 that extends from a proximal end 52P to an opposite distal end 52D thereof, and has whatever length is useful and convenient for its intended use in a hemodialysis machine circuit; a hub 54 that extends longitudinally from an open, proximal end 54P to an open, distal end 54D thereof; a cylindrical, barrel lock 56 that is rotatably and coaxially mounted to, and circumposed about, the proximal end 54P of the hub 54, which barrel lock has an internal thread 56T for mating engagement with the external thread of the first screw lock 14; a stainless steel sleeve 58 that extends longitudinally from a proximal end 58P to an opposite, distal end 58D thereof; a connector 51 disposed within the interior space of the hub for attaching the distal end 58D of the sleeve 58 to the proximal end of the dialysis tubing 52P; and a second, externally threaded screw lock 53 for attaching the distal end 52D of the dialysis extension tubing 52 to a hemodialysis machine circuit (not shown). A portion of the sleeve 58 extends in a proximal direction away from the hub 54 a sufficient distance D for its intended purpose, as discussed below. The extension tubing subassembly 50 is also equipped with an occlusion clamp 55 that occludes the lumen of the extension tubing wherever and whenever it is applied thereto.

FIG. 6 depicts the first embodiment of the invention in the configuration in which it is shipped from a factory of manufacture, sterile packaging removed and ready for use, except that the separate dialysis extension tubing subassembly 50 has been omitted from view. In the configuration depicted in FIG. 6, as assembled at the factory, the needle subassembly 40 is coupled to the housing 12 by extension of the needle 46 through the collapsible tubing 20 with the needle point 46P protruding proximally beyond the catheter lead 22, and by inserting the proximal portion of the adapter 48 and its attached, externally-oriented lug 49 into the open end of the distal portion of housing 12D and its mating, internally-oriented groove 80. This allows the adapter 48 and lug 49 to fit snugly within the confines of the housing and the groove 80. In this condition, by grasping the finger grip 41, a clinician can advance the needle point 46P into a hemodialysis access site. A successful cannulation is confirmed once blood begins to appear in the flashback chamber 44. At that time, the catheter lead 22 is left in the site, and the entire needle assembly 40 is withdrawn from the housing 12, including the needle 46. As the needle is withdrawn from the lumen of the collapsible tubing 20, the pair of spring clips 32, 32 forcibly press inward against opposite sides of the tubing, thereby collapsing the tubing and preventing any further blood flow at that time. Next, the dialysis extension tubing 50 is coupled to the housing 12 by axially inserting a proximal portion of the steel sleeve 58 thereof into the distal end 12D of the housing and thence into the lumen of the collapsible tubing 20, and by threading the barrel lock 56 onto the screw lock 14; see FIG. 9. The distance D by which the sleeve 58 extends proximally from the hub 54, therefore, must be sufficient for the sleeve to extend into the lumen of the collapsible tubing 20 adjacent to the spring clips 32, 32, but not so great as to exceed the length of the collapsible tubing. The proximal end 58P of the steel sleeve 58 must then be flush up against the proximal wall 12P of the catheter housing 12 within the hollow interior 16 of the catheter housing, making a smooth and virtually seamless fit. As the sleeve 58 is advanced into the lumen of the collapsible tubing to a point adjacent to the spring clips 32, 32, the spring clips are forced from their extended, lumen-occluding position back to a retracted position wherein the lumen of the collapsible tubing is no longer occluded, thereby permitting blood to flow from the access site all the way to the occlusion clamp 55. The screw lock 53 is then used to connect the extension tubing subassembly 50 to a dialysis machine circuit. Having completed cannulation at a first hemodialysis site, the process is repeated with a second hemodialysis catheter. To commence dialysis, the dialysis machine is turned on and the occlusion clamps 55 are unpinched from around the dialysis extension tubing 52. To terminate dialysis, the dialysis machine is turned off, the occlusion clamps 55 are again pinched closed over the dialysis extension tubing 52, and the catheter leads 22 are withdrawn from the access sites.

Figure 10:
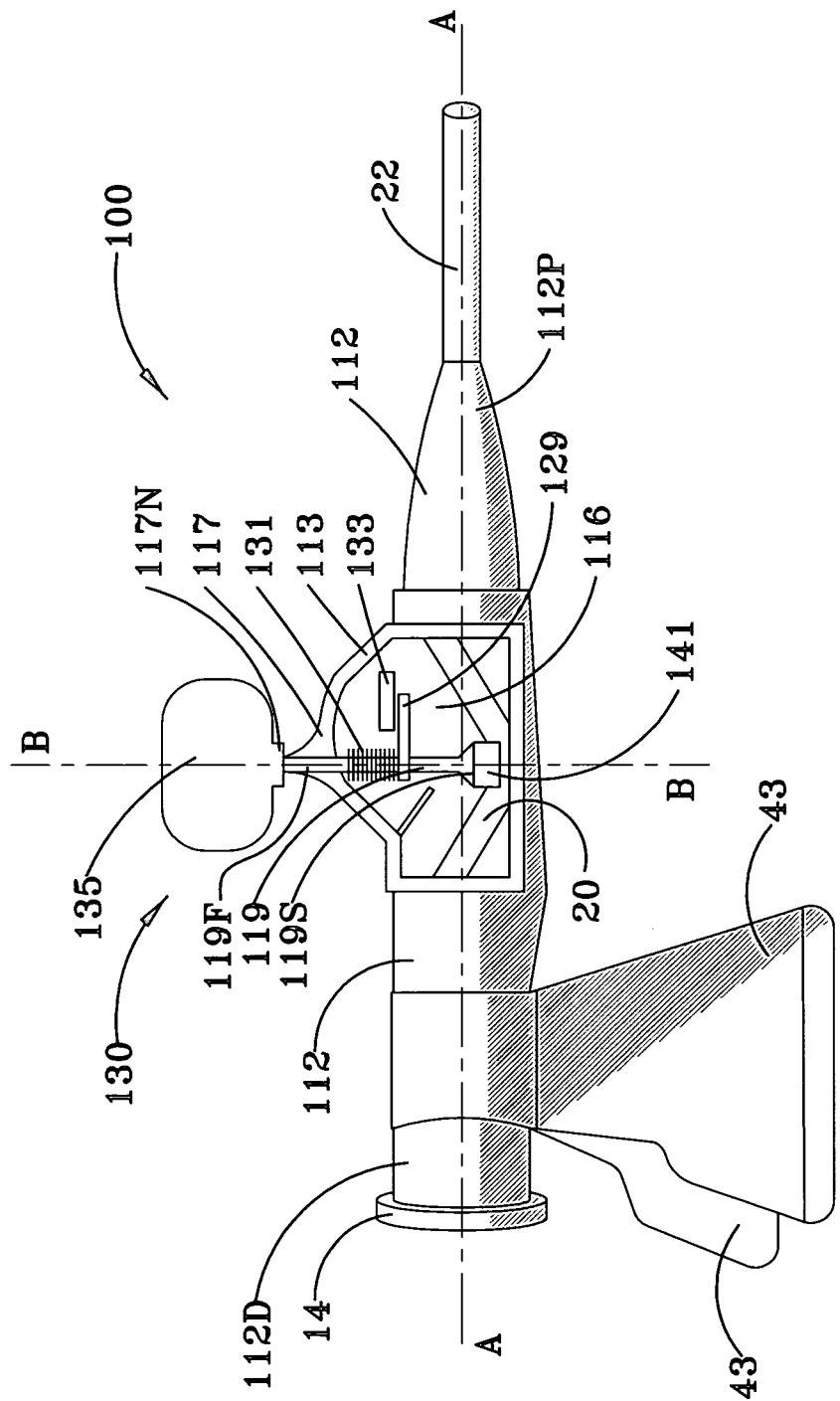
FIG. 10 is right side, elevational view of a second embodiment of the invention, partially cut away to depict the pinch bar in an extended position and forcing the collapse of collapsible tubing within the body portion thereof.
Figure 11:
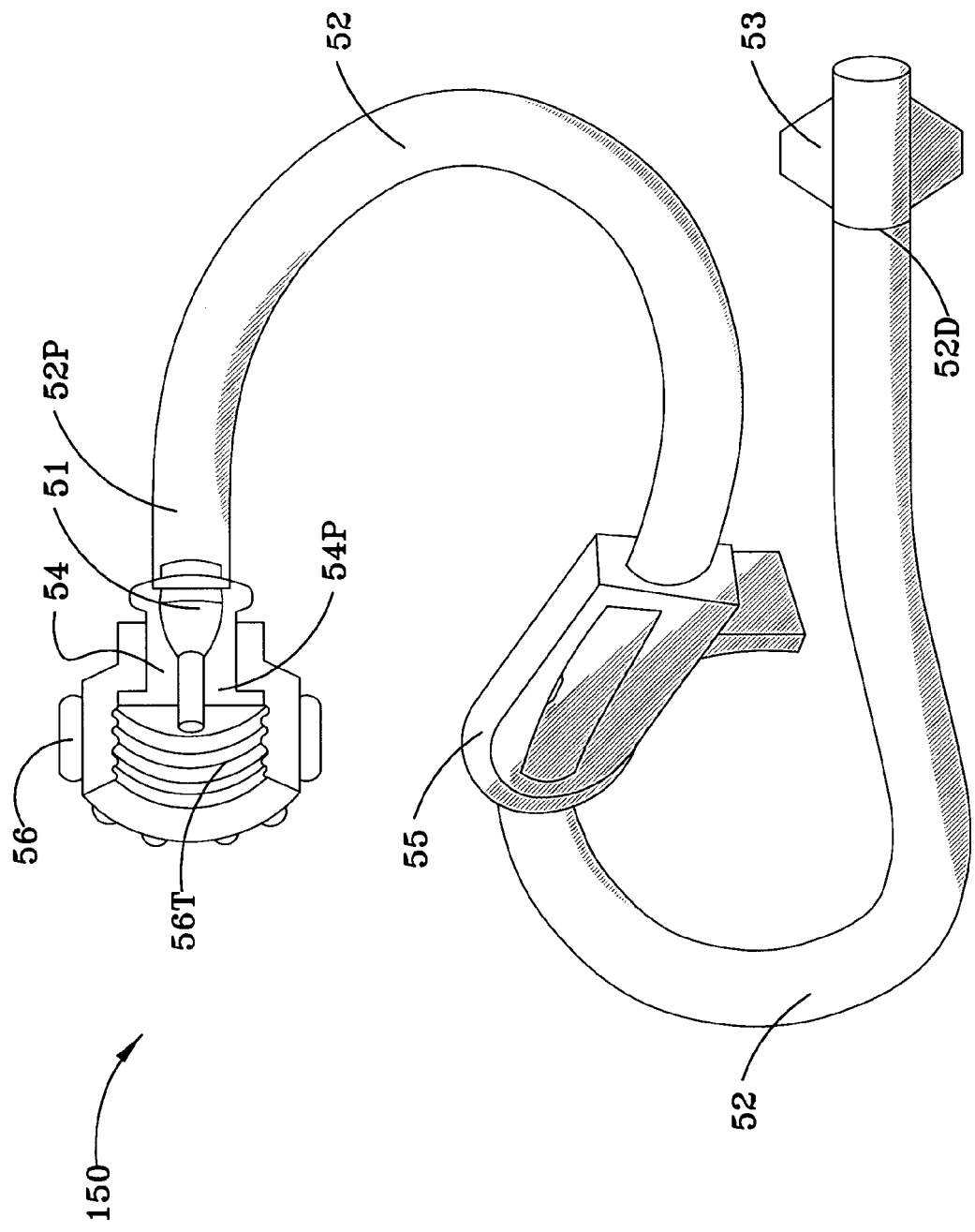
FIG. 11 is a modified extension tubing subassembly for said second embodiment of the invention, which modified subassembly is included in the third and fourth embodiments of the invention as well.

A second embodiment of the present invention will be described hereinafter with respect to FIGS. 10 and 11. In this embodiment of the invention, denoted generally as 100, the component parts of the assembly are the same as in the first embodiment except that the housing 112 and the pinch means 130 thereof have been modified. In a preferred version of the second embodiment, the housing 112 extends along a longitudinal axis A-A from an open, proximal end 112P to an opposite, open, distal end 112D thereof, and has a hollow interior space 116 that communicates with the openings of the proximal and distal ends. The housing 112 has an upper, dome-shaped wall portion 113 that is continuous with the remainder of the housing and extends away from the axis A-A. A raised, cylindrical tunnel 117 extends through the dome-shaped wall portion 113 along an axis B-B normal to axis A-A. The tunnel 117 includes an exterior, upstanding neck portion 117N adjacent to the dome-shaped, wall portion 113 of the housing 112. The pinch means 130 includes a pinch bar 119 that is mounted within the housing 112 for movement between an extended position and a retracted position. The pinch bar 119 extends from a first end 119F through the tunnel 117 to an opposite, second end 119S, and is rotatable and movable within the tunnel between its extended and retracted positions. In its extended position, the second end 119S of the pinch bar 119 engages an exterior surface of the collapsible tubing 20 with sufficient force to collapse and occlude the lumen of the tubing 20; whereas, in its retracted position, the second end 119S is disengaged from the collapsing tubing, the tubing is not collapsed, and the lumen of the tubing is not occluded. As depicted in FIG. 10, the second end 119S of the pinch bar 119 preferably includes a stop block 141 having a broadened end surface for engaging an exterior surface of the compressible tubing 20. A bar lock 129 is rigidly attached to the pinch bar 119 intermediate the first end 119F and second end 119S thereof and extends away from the pinch bar. A coil spring 131 is disposed intermediate, and is compressed between, the bar lock 129 and the domed, upper wall portion 113 of the housing 112, and is circumposed about the pinch bar. Within the interior space 116 of the housing 112, a side latch 133 is attached to the housing 112 and extends part way toward the bar lock 129. Preferably, as depicted in FIG. 10, the side latch 133 is a flat plate that is oriented at an acute angle with respect to axis B-B. Accordingly, so long as the bar lock 129 is rotated around axis B-B away from the side latch 133, the coil spring 131 urges the bar lock 129, and with it the pinch bar 119, towards the collapsible tubing 20 with sufficient force that the pinch bar 119 collapses the collapsible tubing, occludes the lumen thereof, and prevents blood flow. A flexible, hollow, flattened, finger grip 135 covers the first end 119F of the pinch bar 119 and sealingly engages the neck 117N of the tunnel 117 as well. To permit blood flow, a clinician grasps the finger grip 135 and pulls it, together with first end 119F of the pinch bar 119 inside the finger grip, along axis B-B away from the collapsible tubing 20 and rotates them both around said axis until the bar lock 129 comes into contact with the side latch 133, whereupon the finger grip 135 is released and the pinch bar is locked in a retracted position; at the same time, this maneuver leaves the collapsible tubing 20 in an uncollapsed condition and the lumen thereof not occluded. Although just one side latch is depicted in FIG. 10, in like manner additional side latches (not shown) could be included within the interior space 116, distributed about axis B-B. Factory insertion of the needle portion 46 of the needle assembly 40 into the distal end 112D of the housing 112 and through the collapsible tubing 20 will have compressed the coil spring 131 and displaced the stop block 141 along axis B-B and away from axis A-A sufficiently to allow the tubing 20 to remain uncollapsed and the pinch bar 119 to remain in a retracted position.

An advantage of the second embodiment of the invention 100 is that it does not require any extension sleeve to be fixed to a proximal end of the dialysis tubing subassembly. This eliminates any concern for extension sleeve migration if the housing 112 were to be stressed or fractured. Referring now to FIG. 11, it may be seen that a dialysis tubing subassembly 150 for the second embodiment 100 is modified from the dialysis tubing subassembly 50 for the first embodiment 10 in that the sleeve 58 has been eliminated. The proximal end of the connector 51 is slightly extended as a proximal extension and is gradually tapered to facilitate a smooth and virtually seamless connection with the interior of the distal portion 112D of the catheter housing 112. The proximal extension of the connector 51 covers the internal groove 80 within a distal portion of the housing 112 (FIG. 19) and minimizes any turbulence of blood flowing within the lumen of the catheter assembly. A potential disadvantage of the second embodiment 100 is that the second embodiment requires an extra step, as described above, to restore blood flow through the lumen of a hemodialysis catheter.

Figure 14:
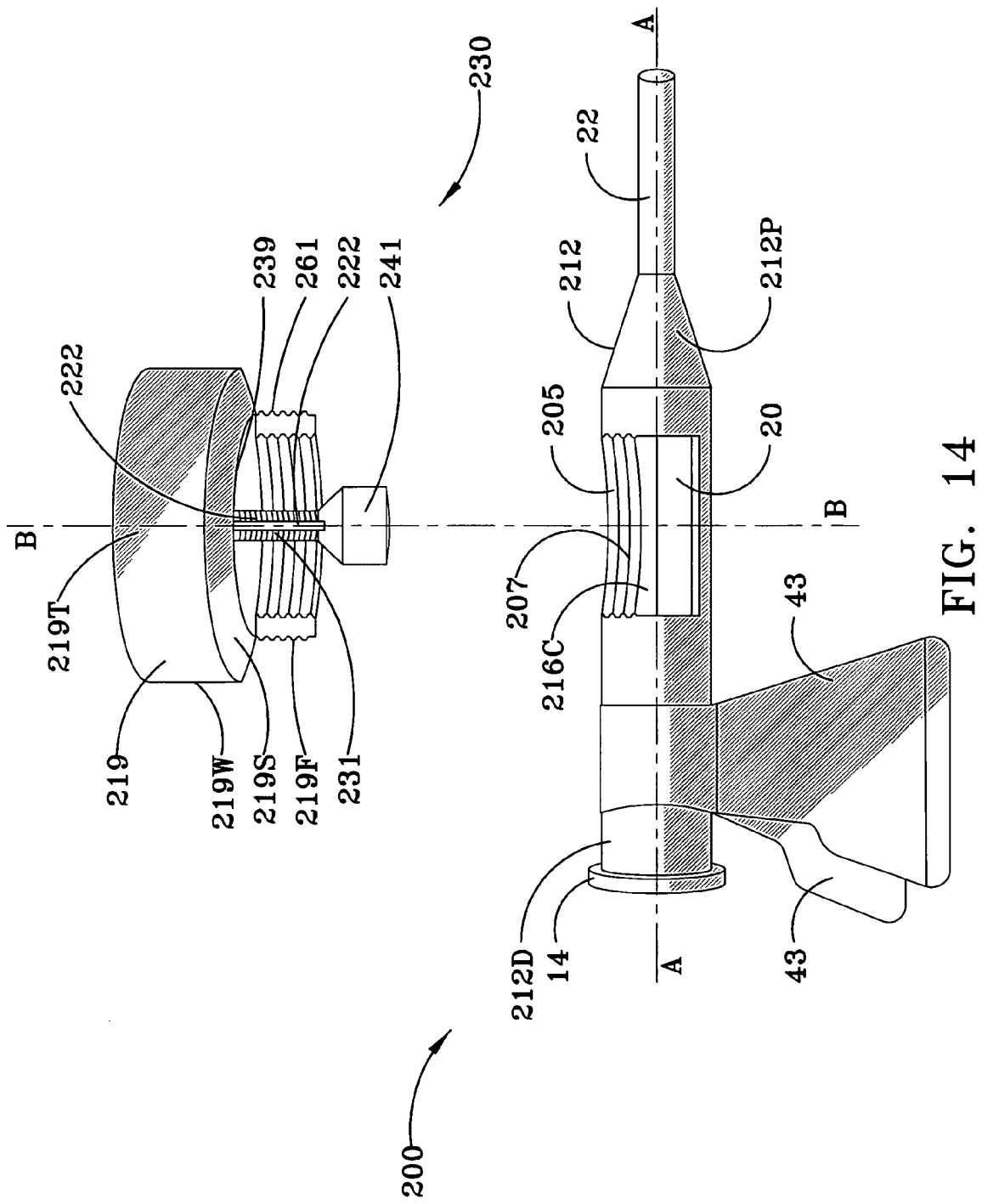
FIG. 14 is a right side elevational view thereof, partially cut away and in partially exploded view along axis B-B.
Figure 17:
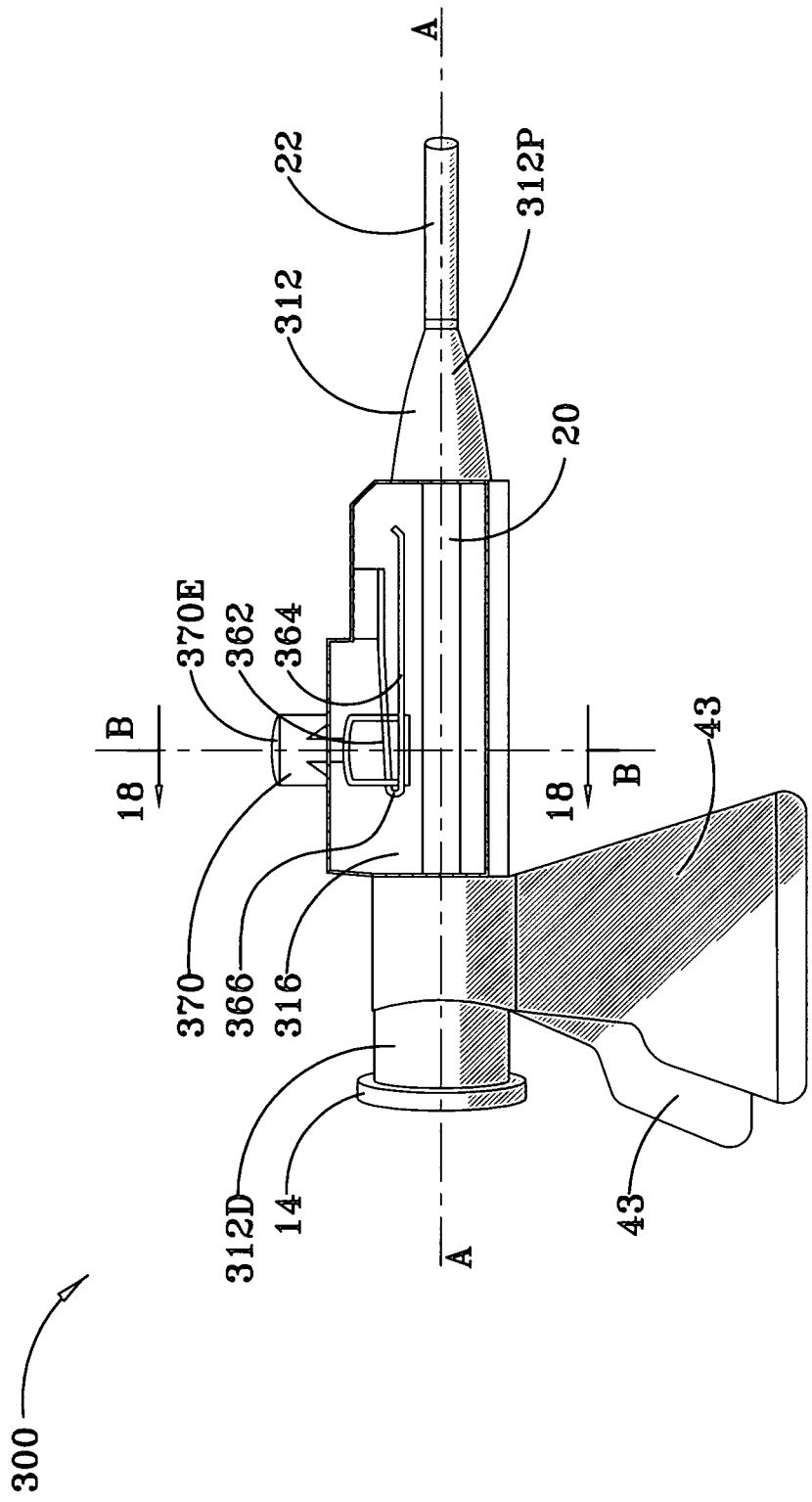
FIG. 17 is a right side, elevational view thereof, showing said tongue in a retracted position and captured within a capture ring, and the collapsible tubing uncollapsed.
Figure 18:
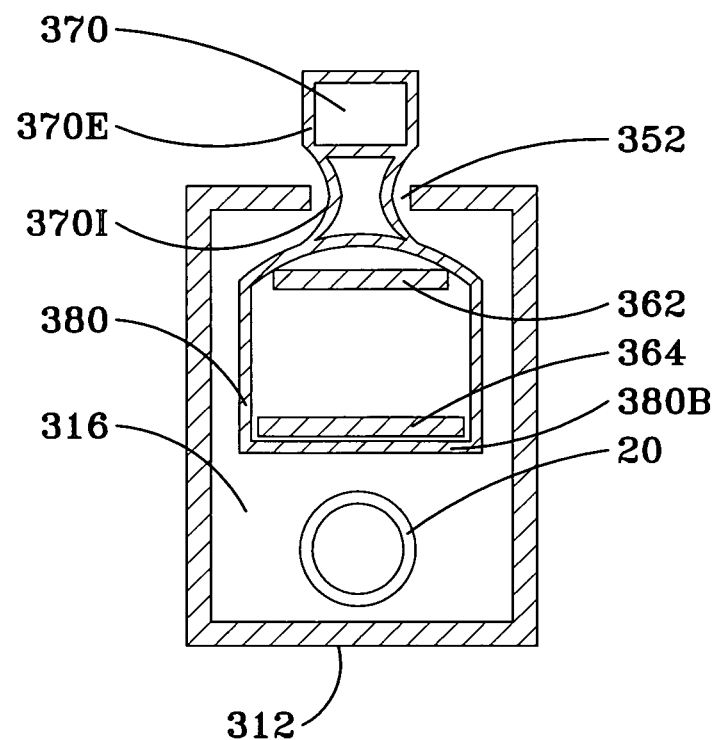
FIG. 18 is an enlarged, cross-sectional view taken along line 18-18 of FIG. 17.

A third embodiment 200 of the present invention will be described hereinafter with respect to FIGS. 12, 13 and 14. The housing 212 of the third embodiment 200 extends longitudinally along an axis A-A from a proximal end 212P to a distal end 212D thereof. The housing 212 has a top wall 212T that is vertically spaced apart from a bottom wall 212B joined by laterally spaced apart, left and right side walls 212L, 212R, respectively. The walls 212T, 212B, 212L, 212R, in combination, define a hollow, distal interior space 216D, a hollow, proximal, interior space 216P, and joining, and in communication with, said spaces, a hollow, substantially cylindrical, central, interior space 216C. The central, interior space 216C is aligned along a transverse axis B-B that is normal to axis A-A and extends from the bottom wall 212B to the top wall 212T. The top wall 212T has a circular, internally threaded, cutout 205 that is centered on, and normal to, axis B-B. As in the case of the first embodiment 10 and the second embodiment 100, collapsible tubing 20 is disposed within said interior spaces of the housing 212 along axis A-A. A screw cap 219 is provided for the housing 212 and has a circular bottom flange 219F that defines a bottom opening of the cap, a circular top wall 219T and a vertical, cylindrical wall 219W that joins the flange to the top wall 219T. The flange 219F has an external thread 261 for mating engagement with the internal thread 207 of the circular cutout 205 of the top wall 212T of the housing 212. The space 239 defined by the top wall 219T, the cylindrical wall 219W, and the flange 219F of the screw cap 219 communicates with the central interior space 216C of the housing 212 whenever the screw cap 219 is threaded into the internal thread 207 of the housing cutout 205.

The pinch means 230 for the third embodiment 200 includes a pinch bar 222 that extends from a first end to an opposite, second end thereof. The second end of the pinch bar 222 includes a stop block 241 having a broadened end face. The first end of the pinch bar 222, together with an adjacent portion of the pinch bar 222, slide into and out of the interior of a narrow tunnel that extends into the interior space 239 of the screw cap 219. A coil spring 231 is disposed intermediate the top wall 219T of the screw cap 219 and the stop block 241 and is circumposed about the pinch bar 222, whereby the coil spring urges the stop block toward the compressible tubing 20. The pinch bar 222 is movable between an extended position, wherein the stop block 241 is pressed by the force of the coil spring 231 against an exterior surface of the collapsible tubing 20 such that the lumen thereof is occluded and blood cannot flow, and a retracted position, wherein the stop block 241 is withdrawn away from the collapsible tubing 20 sufficiently for the tubing to be uncollapsed and its lumen not occluded, so that blood is able to flow. As delivered by a factory of manufacture in sterile packaging to a clinician user, the third embodiment 200 includes a needle subassembly 40, coupled to the distal end of 212D of the housing 212, the screw cap 219 fully threaded into the internally threaded cutout 205, and a flexible, catheter lead 22 extending proximally from a proximal end 212P of the housing, all as previously described in connection with the first embodiment 10; consequently, insertion of the needle portion 46 of the needle subassembly 40 through the compressible tubing 20 at the factory will have compressed the coil spring 231 and forced the stop block 241 to move along axis B-B away from axis A-A sufficiently to uncompress the compressible tubing 20. Accordingly, as it leaves the factory of its manufacture, the pinch bar 222 is in a retracted position. After a successful cannulation at a hemodialysis site, blood will flow through the lumen of the needle 46 and into the flashback chamber 44. Thus assured of a successful cannulation, the clinician uncouples the needle subassembly 40 from the housing 212, thereby withdrawing the needle 46 from the collapsible tubing 20, which allows the coil spring 231 to force the stop block 241 to press against an exterior surface of the collapsible tubing 20, blocking further blood flow. The clinician next couples a dialysis tubing subassembly 150 (described above in connection with the second embodiment 100). Next, the clinician unscrews the screw cap 219 from the cutout 205 of the housing 212, which removes the coil spring 231, and the pinch bar 222 with its attached stop block 241; consequently, the compressible tubing 20 re-expands to an uncompressed condition and the lumen thereof is no longer occluded. The clinician then uses the threaded screw lock 53 of the hemodialysis tubing subassembly 150 to attach the assembly 200 to a dialysis machine circuit, and thereafter uses the occlusion clamp 55 to control blood flow through the assembly.

An advantage of the third embodiment 200 is its relative simplicity: it has few moving parts. Moreover, unlike the first embodiment 10, it does not require an extension sleeve 58 as part of the dialysis extension tubing subassembly 150. A potential disadvantage of the third embodiment 200 is the placement of the screw cap 219, which limits visibility along the length of the housing 212. A second potential disadvantage is the time and effort that is required to unscrew the screw cap after a successful cannulation.

A fourth embodiment 300 of the present invention will be described hereinafter with respect to FIGS. 15, 16, 17, and 18. In this embodiment, a housing 312 extends longitudinally along an axis A-A from an open, proximal end 312P to an opposite, open, distal end 312D. The housing 312 has a hollow, interior space 316 that communicates with the openings of the proximal and distal ends thereof and a first, externally-threaded screw lock 14 attached to, and circumposed about, the distal end 312D. Collapsible tubing 20 extends along axis A-A within the interior space 316 from a proximal end 20P to an opposite, distal end 20D thereof, which ends are attached to the proximal end 312P and the distal end 312D of the housing, respectively. The housing 312 has a slotted opening 352 that extends parallel to axis A-A. Pinch means 330 for the fourth embodiment 300 comprises a tongue 360 and mounting means attached to the housing for mounting the tongue within the interior space 316 of the housing 312 adjacent to the collapsible tubing 20. The tongue 360 includes a base portion 362 attached to the housing 312 and a flexible, resilient, tang portion 364 that is joined to the base portion by a bight portion 366. The base portion 362 extends longitudinally and parallel to axis A-A to the bight portion 366 and can be, as depicted, a straight, flat plate or band. As depicted, the base portion 362 has a proximal end attached to the housing 312 and extends distally to the bight portion 366, but, alternatively, a reverse of that arrangement is also possible—i.e., a distal end of the base portion could be attached to the housing and the base portion could extend proximally to a bight portion 366 (not shown). The tang portion 364 extends longitudinally from the bight portion 366 in a direction substantially parallel to axis A-A, except that the tang portion is progressively sloped along the length thereof toward the collapsible tubing 20. A button 370 is slidably mounted within the slotted opening 352 for movement in a first, proximal direction and in a second, opposite, distal direction, within the slotted opening. The button 370 has an exterior portion 370E that is disposed exterior to the housing 312 and an opposite, interior portion 370I that extends into the interior space 316 of the housing; see FIG. 18. The lateral width of the exterior portion 370E is greater than the lateral width of the slotted opening 352 in order to prevent the button 370 from falling through the slotted opening into the interior space 316 of the housing 312. Attached to, and suspended from, the interior portion 370I of the button 370 is a generally ring-shaped, capture ring 380 that is sized and dimensioned to receive and surround the bight portion 366 of the tongue 360. A bottom portion 380B of the capture ring 380 preferably is flattened for movement into close fitting engagement with the tang portion 364 of the tongue 360. When the button 370 is at or near the distal end 352D of the slotted opening 352, the capture ring 380 is entirely separated from the tongue 360 and the resilient force of the tang portion causes the tang portion to press against an external surface of the collapsible tubing, thereby compressing the tubing and occluding the lumen thereof; in that event, the tongue 360 is in an extended position and blood cannot flow through the collapsible tubing. As the button 370 is moved proximally within the slotted opening 352 from a the distal end 352D thereof, the capture ring 380 progressively surrounds more and more of both the base portion 362 and the tang portion 364 of the tongue 360, which progressively forces the tang portion away from the collapsible tubing 20, thereby permitting the collapsible tubing to become uncollapsed (FIG. 17); in that event, the tongue is in a retracted position, the lumen of the collapsible tubing is not occluded, and blood can flow through the collapsible tubing. It will be understood, of course, that, if the tongue 360 were to be mounted within the housing 312 in a reverse direction, with a distal end 362D of the base portion 362, instead of a proximal end of the base portion, attached to the housing 312, movement of the button 370 within the slotted opening 352 distally from a proximal end 352P thereof would move the tongue from an extended to a retracted position. The fourth embodiment 300 of the invention includes the same dialysis needle subassembly 40 as the first embodiment and the same dialysis extension tubing subassembly 150 as the second embodiment 100, which subassemblies couple to, and uncouple from, the housing 312 in the very same way.

The fourth embodiment 300 of the invention arrives from the manufacturer with the dialysis needle subassembly 40 coupled to the distal end 312D of the housing 312 and the needle 46 inserted within the lumen of the collapsible tubing 20. For as long as the needle 46 remains within the lumen of the compressible tubing 20, the compressible tubing 20 will be reinforced against the resilient force of the tang portion 364 of the tongue 360, which, during cannulation, allows blood to flow through the flexible catheter lead and the compressible tubing into the flashback chamber 44. Next, a clinician uncouples the dialysis needle assembly 40 from the housing 312, thereby withdrawing the needle 46, whereupon the tang portion 364 presses against an exterior surface of the compressible tubing, with sufficient force to occlude the lumen thereof and prevent blood flow. The clinician then couples the dialysis tubing subassembly 150 to the housing 312 and uses the threaded lock 53 to attach the assembly 300 to a dialysis machine circuit. Thereafter, blood flow is controlled with the occlusion clamp 55.

An advantage of the fourth embodiment 300 is ease of use: that is, a sliding button 370 provides a relatively easy way to restore blood flow through the assembly. A potential disadvantage is the need to include within the housing 312 the mechanical components that comprise the pinch means 330 with their potential to malfunction if not properly aligned; and further, that restoring blood flow after successful cannulation requires an additional step compared to the first embodiment 10.

Thus, it should be evident that a dialysis catheter assembly according to the concepts of the present invention has been shown and described in sufficient detail to enable one of ordinary skill in the art to practice the invention. For instance, although other materials might be used, the flexible catheter lead 22 preferably comprises Teflon (registered mark); the housings 12, 112, 212, 312, flexible wings 43, pinch bars 119, 222, spring clips 32, button 370, and capture ring 380, preferably comprise plastic, and the sleeve 58 and hollow needle 46 preferably comprise stainless steel. Since various modifications in details, materials, arrangements of parts, and equivalents thereof, are within the spirit of the invention herein disclosed and described, the scope of the invention should be limited solely by the scope of the claims.

I claim:

1. A hemodialysis catheter assembly, comprising:
   a housing that extends along a longitudinal axis (A-A) from an open, proximal end to an opposite, open, distal end thereof, said housing having a hollow, interior space that communicates with the openings of said proximal and distal ends;
   a first, externally-threaded screw lock attached to, and circumposed about, said distal end;
   collapsible tubing that extends along axis (A-A) within said interior space of the housing from a proximal end to an opposite, distal end thereof, said proximal and distal ends of said tubing being attached to said housing, said tubing comprising a cylindrical wall that defines a lumen, said lumen being in communication with the openings of said proximal and distal ends of said housing;
   a flexible catheter lead, said lead having a distal end attached to the proximal end of the housing and an opposite, free, proximal end, said lead having a lumen in communication with the lumen of said collapsible tubing;
   a dialysis extension tubing subassembly, said subassembly being attachable to the distal end of the housing, and said subassembly including
      dialysis extension tubing that extends from a proximal end to an opposite, distal end thereof;
      a hub that extends longitudinally from an open, proximal end to an open, distal end thereof, said hub defining a hollow interior space;
      a cylindrical, barrel lock rotatably mounted to, and circumposed about, the proximal end of said hub, said barrel lock having an internal thread for mating engagement with the external thread of said first screw lock; and
      a second, externally-threaded screw lock attached to the distal end of the dialysis extension tubing for connecting said extension tubing to a hemodialysis machine circuit;
      a sleeve that extends longitudinally from a proximal end to an opposite, distal end thereof, a distal portion of said sleeve being disposed within the interior space of the hub and a portion of said sleeve extending a distance D proximally away from the hub;
      connector means disposed within the interior space of the hub for attaching the distal end of said sleeve to the proximal end of said dialysis extension tubing, thereby to place the lumen of said sleeve in communication with the lumen of said extension tubing;
   a hemodialysis needle subassembly, said subassembly including
      a barrel that extends longitudinally from an open, proximal end to an opposite, open, distal end, said barrel having a hollow, interior space that communicates with said proximal and distal ends;
      a hollow, flashback chamber attached to the distal end of the barrel, said chamber comprising a cap that completely covers and closes off said distal end, said chamber including a semipermeable membrane to permit air, but not blood, to escape whenever blood enters into the chamber, and at a least a portion of said chamber being transparent in order to permit visual monitoring of entry of blood into the chamber;
      a hollow needle having a distal end and an opposite, proximal end, said proximal end comprising a sharpened, bevel point;
      a needle adapter that extends longitudinally from an open, proximal end to an opposite, open, distal end thereof, said adapter having a longitudinal bore that extends from said proximal end to said distal end, wherein the proximal end of said needle extends away from the proximal end of the adapter and the distal end of said needle is inserted into, and retained within a proximal portion of said bore of said adapter, such that the lumen of the needle is in communication with the hollow, interior space of said barrel and with said flashback chamber, and a proximal end of said adapter is shaped and dimensioned for close fitting retention within a distal portion of the hollow, interior space of the housing; and pinch means disposed intermediate the proximal and distal ends of said collapsible tubing within the interior space of the housing at a distance less than or equal to D from the distal end of the housing, said pinch means being alterable between a normally pinched condition wherein a portion of the wall of said collapsible tubing is collapsed inwardly and sufficiently to occlude and prevent blood flow through said collapsible tubing, and an unpinched condition wherein the lumen of said collapsible tubing is not occluded, said pinch means comprising a pair of spring clips attached to the interior of the housing and on opposite sides of said collapsible tubing, said clips being movable between a first, pinched position in which the clips press toward each other and against said opposite sides of said collapsible tubing with sufficient force to collapse said collapsible tubing and occlude the lumen thereof if said needle and said sleeve are not present within said lumen, and a second, retracted position in which said collapsible tubing is not collapsed and the lumen thereof is not occluded, said second, retracted position being obtainable by axial insertion of either said needle or said sleeve into the lumen of said collapsible tubing.

2. The assembly of claim 1, further comprising an upstanding finger grip attached to the barrel to facilitate maneuvering the needle into engagement with an access site on the body of a hemodialysis patient.

3. The assembly of claim 2, wherein the interior space of the housing is defined in part by an interior wall, a groove in said wall extends longitudinally and proximally from the distal, open end of the housing, and the adapter has a raised lug that fits tightly within said groove.

4. The assembly of claim 3, further comprising a pair of laterally and oppositely directed, flexible wings attached to the housing to facilitate attaching the housing to a hemodialysis patient adjacent to a hemodialysis access site.

5. The assembly of claim 4, wherein the finger grip includes a pair of spaced apart prongs adapted for receiving and storing therebetween said pair of wings when said wings are not in use.

* * * * *